(12) United States Patent
Zhang et al.

(10) Patent No.: US 10,722,148 B2
(45) Date of Patent: Jul. 28, 2020

(54) FALL DETECTION DEVICES, SYSTEMS, AND METHODS

(71) Applicant: Florida State University Research Foundation, Inc., Tallahassee, FL (US)

(72) Inventors: Zhenghao Zhang, Tallahassee, FL (US); Avishek Mukherjee, Tallahassee, FL (US); Subhankar Banerjee, Tallahassee, FL (US)

(73) Assignee: Florida State University Research Foundation, Inc., Tallahassee, FL (US)

( * ) Notice: Subject to any disclaimer, the term of this patent is extended or adjusted under 35 U.S.C. 154(b) by 0 days.

(21) Appl. No.: 16/169,028

(22) Filed: Oct. 24, 2018

(65) Prior Publication Data

US 2019/0117125 A1   Apr. 25, 2019

Related U.S. Application Data

(60) Provisional application No. 62/576,219, filed on Oct. 24, 2017.

(51) Int. Cl.

| A61B 5/11 | (2006.01) |
|---|---|
| G08B 21/04 | (2006.01) |
| A61B 5/00 | (2006.01) |
| A61B 5/1495 | (2006.01) |
| A61B 5/01 | (2006.01) |
| G08B 13/19 | (2006.01) |
| G01P 13/00 | (2006.01) |
| G01P 15/00 | (2006.01) |

(52) U.S. Cl.
CPC ............ *A61B 5/1117* (2013.01); *A61B 5/002* (2013.01); *A61B 5/0022* (2013.01); *A61B 5/0077* (2013.01); *A61B 5/015* (2013.01); *A61B 5/1116* (2013.01); *A61B 5/1118* (2013.01); *A61B 5/1495* (2013.01); *A61B 5/6889* (2013.01); *A61B 5/7264* (2013.01); *A61B 5/747* (2013.01); *G08B 13/19* (2013.01); *G08B 21/043* (2013.01); *G08B 21/0446* (2013.01); *G08B 21/0461* (2013.01); *A61B 2560/0252* (2013.01); *G01P 13/00* (2013.01); *G01P 15/00* (2013.01)

(58) Field of Classification Search
CPC ..... A61B 5/1117; A61B 5/747; G08B 21/043; G08B 21/0446
See application file for complete search history.

(56) References Cited

U.S. PATENT DOCUMENTS

| 8,115,641 B1 * | 2/2012 | Dempsey | G08B 21/0492 340/522 |
|---|---|---|---|
| 2007/0159332 A1 * | 7/2007 | Koblasz | G06F 19/3418 340/572.1 |
| 2013/0335550 A1 * | 12/2013 | Rochenski | G08B 17/125 348/82 |

OTHER PUBLICATIONS

Alwan et al., "A Smart and Passive Floor-Vibration Based Fall Detector for Elderly," IEEE, 2006, pp. 1003-1007.

(Continued)

*Primary Examiner* — Curtis B Odom
(74) *Attorney, Agent, or Firm* — Eversheds Sutherland (US) LLP

(57) ABSTRACT

Provided herein are systems and devices capable of detecting an event, such as the fall of a human. The devices may include a motion sensor, a heat sensor, and a vibration sensor. The devices and systems also may include an alarm and/or communication device configured to function when the event occurs.

2 Claims, 25 Drawing Sheets

(56) References Cited

OTHER PUBLICATIONS

Debard et al., "Camera-Based Fall Detection Using a Particle Filter," IEEE, 2015, pp. 6947-6950.
Garripoli et al., "Embedded DSP-Based Telehealth Radar System for Remote In-Door Fall Detection," IEEE Journal of Biomedical and Health Informatics, 2015, 19(1):92-101.
Khan et al., "Review of Fall Detection Techniques: A Data Availability Perspective," Medical Engineering and Physics, 2017, 39:12-22.
Li et al., "Efficient Source Separation Algorithms for Acoustic Fall Detection Using a Microsoft Kinect," IEEE Transactions on Biomedical Engineering, 2014, 61(3):745-755.
Mastorakis et al., "Fall Detection System Using Kinect's Infrared Sensor," J Real-Time Image Proc, 2014, 9:635-646.
Portmann et al., "People Detection and Tracking from Aerial Thermal Views," IEEE International Conference on Robotics & Automation, 2014, pp. 1794-1800.
Skubic et al., "Testing Non-Wearable Fall Detection Methods in the Homes of Older Adults," IEEE, 2016, pp. 557-560.
Sposaro et al., "iFall: An Android Application for Fall Monitoring and Response," 31st Annual International Conference of the IEEE EMBS, 2009, pp. 6119-6122.
Wang et al., "WiFall: Device-Free Fall Detection by Wireless Networks," IEEE Transactions on Mobile Computing, 2017, 16(2):581-594.
Zigel et al., "A Method for Automatic Fall Detection of Elderly People Using Floor Vibrations and Sound—Proof of Concept on Human Mimicking Doll Falls," IEEE Transactions on Biomedical Engineering, 2009, 56(12):2858-2867.

\* cited by examiner

FALL DETECTION DEVICES, SYSTEMS, AND METHODS

CROSS-REFERENCE TO RELATED APPLICATIONS

This application claims priority to U.S. Provisional Patent Application No. 62/576,219, filed Oct. 24, 2017, which is incorporated herein by reference.

STATEMENT REGARDING FEDERALLY SPONSORED RESEARCH OR DEVELOPMENT

This invention was made with government support under contract numbers 1149344 and 1618358 awarded by the National Science Foundation. The government has certain rights in the invention.

BACKGROUND

It is known that a significant percentage of falls, especially among senior adults, cause serious injuries, such as broken bones or head injuries. Currently, there are many companies offering fall detection services. However, most, if not all, commercial systems require the user to wear a device, which can be inconvenient. Many attempts have been made to detect falls with systems that do not include wearable devices. These systems have included or relied on depth cameras, sound detectors, radar and radio frequency (RF) signals, floor vibration, etc. Each of these prototypes, however, suffers from one or more limitations, including, but not limited to, low accuracy in certain scenarios, high cost, and/or a lack of security (i.e., privacy concerns).

A system was tested in the homes of senior adults, which used a combination of Doppler radar, a Microsoft KINECT® sensor, and a webcam for fall detection. The results prompted further study of the use of the Microsoft KINECT® sensor, but the system (i) was susceptible to sudden light changes, and, therefore, had difficulty detecting falls occurring at such moments, and (ii) was costlier and/or less acceptable to users with security (e.g., privacy) concerns.

There remains a need for devices and/or systems that can detect falls accurately, are affordable, do not raise substantial security (e.g., privacy) concerns, do not rely on training data that may be difficult to obtain, including high-quality training data, and/or do not include a wearable component.

BRIEF SUMMARY

Provided herein are fall detection devices and systems, which may address one or more of the foregoing needs. For example, embodiments of the devices and systems provided herein do not require the human to wear any component of the devices and systems. As a further example, the devices and systems may achieve excellent performance, by detecting falls accurately and eliminating or significantly reducing false alarms. As yet another example, the devices and systems provided herein may be constructed with relatively inexpensive components.

In some embodiments, the devices include a device body having a base configured to be placed on a surface; a vibration sensor configured to detect vibrations of the surface; a motion sensor; a heat sensor; and a processing unit configured to (i) receive one or more signals from each of the motion sensor, the heat sensor, and the vibration sensor, and (ii) determine the occurrence of an event in view of the one or more signals received from the motion sensor, the heat sensor, and the vibration sensor; wherein the vibration sensor, the heat sensor, the motion sensor, and the processing unit are housed by the device body.

In some embodiments, the devices include a device body having a base configured for placement on a surface; a vibration sensor configured to detect vibrations of the surface; a motion sensor including a receiver configured to received transmissions from one or more radio frequency transmitters; a heat sensor including a thermal camera, wherein the thermal camera comprises a plurality of pixels; and a processing unit configured to (i) receive one or more signals from each of the motion sensor, the heat sensor, and the vibration sensor, and (ii) determine an occurrence of an event based on the one or more signals received from the motion sensor, the heat sensor, and the vibration sensor; wherein the motion sensor, the heat sensor, the vibration sensor, and the processing unit are housed by the device body.

In another aspect, systems are provided. In some embodiments, the systems include [1] a device, wherein the device includes a device body having a base configured to be placed on a surface; a vibration sensor configured to detect vibrations of the surface; a motion sensor; a heat sensor; and a processing unit configured to (i) receive one or more signals from each of the motion sensor, the heat sensor, and the vibration sensor, and (ii) determine the occurrence of an event in view of the one or more signals received from the motion sensor, the heat sensor, and the vibration sensor; wherein the vibration sensor, the heat sensor, the motion sensor, and the processing unit are housed by the device body; and [2] one or more transmitters. The one or more transmitters may include one or more radio frequency transmitters.

In another aspect, methods for determining the occurrence of a fall of a human are provided. In some embodiments, the methods include providing a system as described herein; detecting a motion-to-stationary transition of the human with the motion sensor; estimating a distance of the human from the heat sensor by determining a fraction of the plurality of pixels that detect a body temperature of the human; determining whether the human is standing after the motion-to-stationary transition based on a signal from the heat sensor; and declaring the occurrence of the fall if—[1] (i) the human is not standing after the motion-to-stationary transition, and (ii) a signal from the vibration sensor is greater than a threshold value based on the distance of the human from the heat sensor; or [2] (i) the signal from the heat sensor indicates that the human is standing after the motion-to-stationary transition, (ii) no movement is detected by the system for at least 10 seconds after the motion-to-stationary transition, and (iii) a signal from the vibration sensor is greater than a threshold value based on the distance of the human from the heat sensor.

In some embodiments, the methods include providing a system as provided herein; detecting a motion-to-stationary transition with the motion sensor; estimating a distance of the human from the heat sensor by comparing a first signal and a second signal received by the processing unit from the heat sensor before and after the motion-to-stationary transition, respectively; determining whether the second signal indicates that the human is standing after the motion-to-stationary transition; and declaring the occurrence of the fall if (i) the human is not standing, and (ii) a third signal from the vibration sensor is greater than a threshold value based on the distance of the human from the heat sensor.

DETAILED DESCRIPTION

Figure 1:
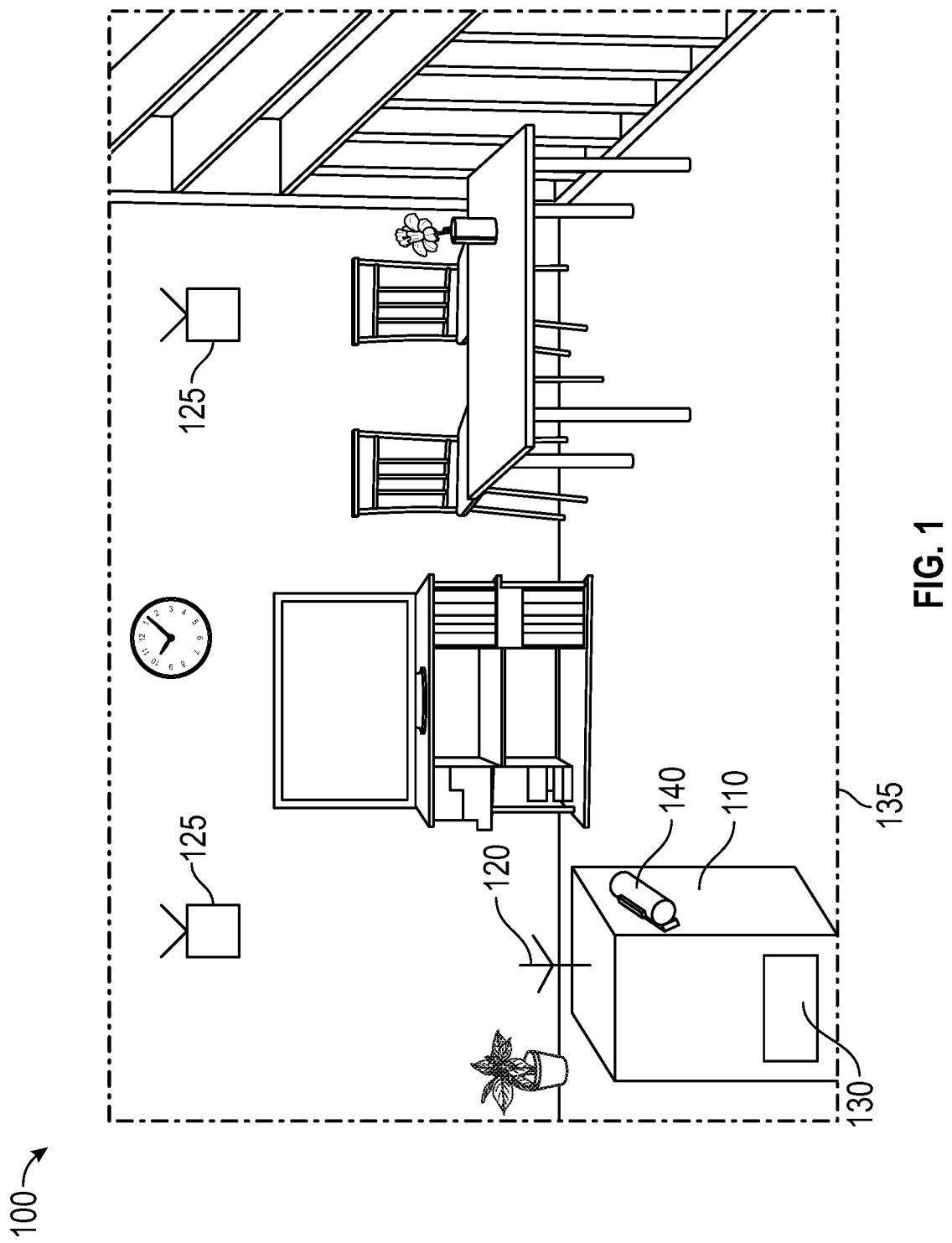
FIG. 1 depicts an embodiment of a system described herein.

Embodiments of the devices and systems herein can achieve high performance by processing signals from different types of sensors, which can complement each other and enable simple, yet robust, rules to detect the occurrence of falls.

In some embodiments, the devices herein do not depend on any training data, including training data that is obtained through humans falling in different manners. Instead, the devices may follow logic based on the well-understood characteristics of falls, such as a motion-to-stationary transition and floor vibration, which should be observed for most, if not all, falls. This is in contrast with other fall detection devices and algorithms, which typically use machine learning techniques to classify the activities.

Devices

In one aspect, devices are provided. In some embodiments, the devices include a device body, a vibration sensor, a motion sensor, a heat sensor, and a processing unit. The device body may be configured to house one or more of the vibration sensor, the motion sensor, the heat sensor, and the processing unit.

Not wishing to be bound by any particular theory, it is believed that the inclusion of three different types of sensors can permit better performance and/or correct estimations. For example, one feature of a fall observed by a motion sensor may be a motion period followed by a stationary period, corresponding to the action during the fall and the inactivity after the fall. However, very similar motions can occur during many other events, such as a sit event. Due to the inclusion of a vibration sensor in embodiments of the devices herein, however, fall and sit events can be distinguished, because the latter does not produce the same level of floor vibration as the former.

In some embodiments, the device body houses the vibration sensor, the motion sensor, the heat sensor, and the processing unit. A device body "houses" a component, when a component is (i) arranged in the device body, (ii) arranged on the device body, or (iii) connected to the device body (e.g., by a cable, a support, etc.).

The device body, in some embodiments, includes a base configured to be placed on a surface. The surface may be a floor, including a carpeted floor, a hard wood floor, a tile floor, a linoleum floor, etc. The base of the device body may include one or more portions that contact the surface, and permit the device to retain a desired position while in use, including, but not limited to, an upright position.

The device body generally may have any dimensions. In some embodiments, the device body has dimensions that permit one or more of the components housed by the device body to be positioned at a desirable location, spaced a desirable distance from one or more of the other components, or a combination thereof.

The device body may be made of any material, including, but not limited to, a plastic, a metal, a ceramic, or a combination thereof.

Vibration Sensors

The devices herein may include a vibration sensor. In some embodiments, a vibration sensor is housed by a device body. In some embodiments, a vibration sensor is configured to measure the vibrations of a surface, including the surface on which a base of a device body is configured to be placed.

In some embodiments, the vibration sensor includes a seismograph. The vibration sensor may be configured to report a vibration reading at a desired time increment. For example, the vibration sensor may be configured to report a vibration reading every 20 ms. Other time increments, however, are envisioned. In some embodiments, the time increment is about 5 ms to about 100 ms, about 10 ms to about 50 ms, about 10 ms to about 40 ms, or about 10 ms to about 30 ms.

Motion Sensors

The devices provided herein may include a motion sensor. In some embodiments, the motion sensor includes a receiver configured to receive transmissions from one or more radio frequency transmitters.

In some embodiments, the motion signal(s) detected by a motion sensor is based on the changes of an electromagnetic field caused by one or more movements, including human movements. The motion signal may be collected by a radio frequency receiver of a motion sensor. The motion sensor may monitor the radio frequency signal(s) emitted by one or more transmitters, including small ultra-low power radio frequency transmitters, which may be referred to herein as "tags."

Heat Sensors

The devices provided herein may include a heat sensor. In some embodiments, the heat sensor includes a thermal camera. The heat sensor, such as the thermal camera, may include a plurality of pixels. As used herein, the phrase "plurality of pixels" may refer to an array of more than two pixels.

The heat sensors may be configured to estimate a distance of a human from the heat sensors by determining the fraction of the plurality of pixels that detect a body temperature. As used herein, the phrase "body temperature" refers to the body temperature of a human, which typically is about 37° C., but may be about 35° C. to about 39° C.

The heat sensors may be able to determine whether a human is standing before and/or after a motion-to-stationary event. For example, a signal from a heat sensor may indicate that at least a fraction of its plurality of pixels detects a body temperature prior to a motion-to-stationary event, and, after the motion-to-stationary event, the signal from the heat sensor may indicate that the fraction of its plurality of pixels that detects a body temperature has decreased or that none of the pixels detects a body temperature, thereby indicating that the human is no longer standing.

In some embodiments, the heat sensor includes a thermal camera, and the thermal camera includes 40 pixels to 80 pixels. In some embodiments, the heat sensor includes a thermal camera, and the thermal camera includes 64 pixels.

The pixels of the heat sensor may have any spanning angle. In some embodiments, each pixel has a spanning angle of about 7.5 degrees.

In some embodiments, the heat sensor may be housed by a device in a manner that ensures that the heat sensor and the surface are spaced a desirable distance apart. In some embodiments, the distance between the heat sensor and the surface is about 0.5 meters. In some embodiments, the distance between the heat sensor and the surface is at least 0.5 meters.

When the heat sensor includes a thermal camera, the thermal camera, in some embodiments, may be pointed upward relative to the device at an angle of about 40 degrees to about 70 degrees relative to the surface on which a device is placed. In some embodiments, the heat sensor pointed upwards at an angle of about 60 degrees relative to the surface on which a device is placed.

Processing Unit

The devices provided herein may include a processing unit. The processing unit, in some embodiments, is configured to (i) receive one or more signals from each of the motion sensor, the heat sensor, and the vibration sensor, and (ii) determine the occurrence of an event in view of the signals received from the motion sensor, the heat sensor, and the vibration sensor.

In some embodiments, the event for which the occurrence is determined is a fall of a human. The devices and systems herein, however, may be configured to determine the occurrence of one or more other events.

Accessories

In some embodiments, the devices provided herein also include an alarm configured to emit a sound when the processing unit determines the occurrence of the event. For example, if a device determines that a human has fallen, then an alarm may emit a sound to alert another person that a fall has occurred.

In some embodiments, the devices provided herein also include a communication device configured to communicate the occurrence of the event. For example, if a device determines that a human has fallen, then the device may communicate to another person (e.g., a family member, neighbor, emergency operator, etc.) via any communication device (e.g., phone, intercom, pager, etc.) that a fall has occurred.

Systems

In one aspect, systems are provided. The systems generally may include any one or more of the devices herein, and one or more transmitters. The one or more transmitters may include radio frequency transmitters.

In some embodiments, the one or more transmitters are radio frequency transmitters, and the radio frequency transmitters are wireless ultra-low power radio frequency transmitters. In some embodiments, the system includes one radio frequency transmitter. In some embodiments, the system includes two radio frequency transmitters.

The one or more radio frequency transmitters may be configured to transmit signals with a pulse interval modulation.

The one or more transmitters, in some embodiments, are placed at least about 1 meter above the surface on which a device is placed. For example, the one or more transmitters may be hung on a wall at a position that is at least about 1 meter above the surface on which a device is placed.

In some embodiments, the one or more transmitters transmit a signal to the motion sensor at a certain time increment. In some embodiments, the one or more transmitters transmit a signal to a motion sensor, on average, every 200 ms, with a random time offset to avoid consistently "colliding" with another transmitters. The transmitters, in some embodiments, transmit a burst of 10 pulses, wherein each pulse is about 40 µs.

Methods

Also provided herein are methods for detecting an occurrence of a fall of a human.

In some embodiments, the methods include providing a system as described herein; detecting a motion-to-stationary transition of the human with the motion sensor; estimating a distance of the human from the heat sensor by determining a fraction of the plurality of pixels that detect a body temperature of the human; determining whether the human is standing after the motion-to-stationary transition based on a signal from the heat sensor; and declaring the occurrence of the fall if—[1] (i) the human is not standing after the motion-to-stationary transition, and (ii) a signal from the vibration sensor is greater than a threshold value based on the distance of the human from the heat sensor; or [2] (i) the signal from the heat sensor indicates that the human is standing after the motion-to-stationary transition, (ii) no movement is detected by the system for at least 10 seconds after the motion-to-stationary transition, and (iii) a signal from the vibration sensor is greater than a threshold value based on the distance of the human from the heat sensor.

In some embodiments, the methods include declaring the occurrence of the fall if—[1] (i) the human is not standing after the motion-to-stationary transition, and (ii) a signal from the vibration sensor is greater than a threshold value based on the distance of the human from the heat sensor; or [2] (i) the signal from the heat sensor indicates that the human is standing after the motion-to-stationary transition, (ii) no movement is detected by the system for about 10 seconds to about 120 seconds after the motion-to-stationary transition, and (iii) a signal from the vibration sensor is greater than a threshold value based on the distance of the human from the heat sensor.

In some embodiments, the methods include declaring the occurrence of the fall if—[1] (i) the human is not standing after the motion-to-stationary transition, and (ii) a signal from the vibration sensor is greater than a threshold value based on the distance of the human from the heat sensor; or [2] (i) the signal from the heat sensor indicates that the human is standing after the motion-to-stationary transition, (ii) no movement is detected by the system for about 20 seconds to about 40 seconds after the motion-to-stationary transition, and (iii) a signal from the vibration sensor is greater than a threshold value based on the distance of the human from the heat sensor.

In some embodiments, the methods include declaring the occurrence of the fall if—[1] (i) the human is not standing after the motion-to-stationary transition, and (ii) a signal from the vibration sensor is greater than a threshold value based on the distance of the human from the heat sensor; or [2] (i) the signal from the heat sensor indicates that the human is standing after the motion-to-stationary transition, (ii) no movement is detected by the system for about 30 seconds after the motion-to-stationary transition, and (iii) a signal from the vibration sensor is greater than a threshold value based on the distance of the human from the heat sensor.

In some embodiments, the methods include providing any of the systems provided herein; detecting a motion-to-stationary transition of a human with the motion sensor; estimating a distance of the human from the heat sensor by comparing a first signal and a second signal received by the processing unit from the heat sensor before and after the motion-to-stationary transition, respectively; determining whether the second signal indicates that the human is standing after the motion-to-stationary transition; and declaring the occurrence of the fall if (i) the human is not standing, and (ii) a third signal from the vibration sensor is greater than a threshold value based on the distance of the human from the heat sensor. In some embodiments, the threshold value increases as the estimated value of the distance of the human from the heat sensor decreases.

The declaring of the occurrence of the fall may include sounding an alarm, communicating the occurrence via a communication device, or a combination thereof.

The present invention is further illustrated by the following examples, which are not to be construed in any way as imposing limitations upon the scope thereof. On the contrary, it is to be clearly understood that resort may be had to various other aspects, embodiments, modifications, and equivalents thereof which, after reading the description herein, may suggest themselves to one of ordinary skill in the art without departing from the spirit of the present invention or the scope of the appended claims. Thus, other aspects of this invention will be apparent to those skilled in the art from consideration of the specification and practice of the invention disclosed herein.

EXAMPLES

In the following examples, embodiments of the devices and systems provided herein were evaluated in realistic environments including a living room and a bathroom. The evaluations performed in the following examples included [1] False Negative tests, [2] False Positive daily use tests, and [3] False Positive stress tests.

For the False Negative tests, a human test subject fell in different manners in different rooms to determine if an embodiment of the device could correctly detect the falls of the human test subject.

For the False Positive daily use tests, the system was run for 24 hours in a room with a human conducting normal activities to determine if the embodiment of the system incorrectly detected a fall of the human.

For the False Positive stress tests, a selected set of activities other than falls was repeated to determine whether an embodiment of a device could correctly determine that the selected set of activities did not include a fall.

As explained in the following examples, the embodiment of the system tested caused no false negatives or false positives in the "daily use test", and in the false positive stress test only two non-fall activities were detected. The two non-fall activities, however, were activities that are unlikely to be performed by humans of advanced age.

Example 1—Device and System

In this example, one device was placed in a room having a size of about 16 square meters. More than one device may be used in a room, especially rooms larger than 16 square meters. The device of this example collected three types of signals: the motion signal, the heat signal, and the floor vibration signal.

FIG. 1 depicts the embodiment of the system 100 tested in this example. The system 100 included a device 110 arranged on the floor 135 of a room. The device 110 included an RF receiver 120, which monitored the RF signals emitted by two RF transmitters 125 hanging on a wall of the room. The device 110 also included a heat sensor 140, and a vibration sensor 130. The vibration sensor 130 was configured to detect vibrations of the floor 135 of the room.

The motion signal was based on the changes of an electromagnetic field caused by one or more human movements. The motion signal of this example was collected by an RF receiver inside the device, which monitored the RF signal emitted by two small ultra-low power RF transmitters, called tags, placed in the same room. It should be noted, however, that other numbers of tags may be used in other systems (e.g., one tag, or three or more tags).

The heat sensor and the vibration sensor were part of the device of this example. To avoid or minimize incorrect readings of the heat sensor, the device was placed as far as possible from any heat source in the room. Examples of heat sources can include stoves, heaters, air conditioners, etc., and, in this example, there were no obstructions that might block the heat sensor. In other words, there were no possible obstructions within 1 meter of the heat sensor.

In this example, the device was placed on the floor of the room to detect the floor vibration. The device included a processing unit, which was a Raspberry Pi, and other circuits.

Motion Detection Module:

The MD module was based on an RF signal. In this example, it included a receiver and two transmitters called tags operating in the 433 MHz band.

The receiver of this example was implemented with inexpensive low bandwidth software defined radios, and the tags were implemented with programmable wireless modules.

The tags of this example periodically transmitted their IDs, and the receiver demodulated the RF signal and considered whether there was motion when the fluctuation of the wireless channel was above a particular level, and otherwise stationary.

Implementation of MD Module:

Effort was made to extend the battery life of the tags, because, in practice, it may be desirable to place at least one of the tags at a location with no power outlets, such as a shower room, or no easily accessible power outlets.

Therefore, an ultra-low power design based on pulse interval modulation was adopted for the tags of this example. Similar tags have been used in some active RFIDs, and the RFIDs lasted for 2-3 years on a single coin cell battery while transmitting the ID every 2 seconds.

In this example, the tags transmitted their ID, on average, every 200 ms, with some random time offset to avoid consistently interfering with another tag. The tags basically transmitted a burst of 10 pulses, wherein each pulse was very short (40 μs). The tag identity information was represented by the intervals between the pulses, which was the signature of each tag. The signatures were unique to each tag, and were based on preselected pseudo random numbers, ranging from about 1.5 ms to about 2.5 ms.

Figure 2A:
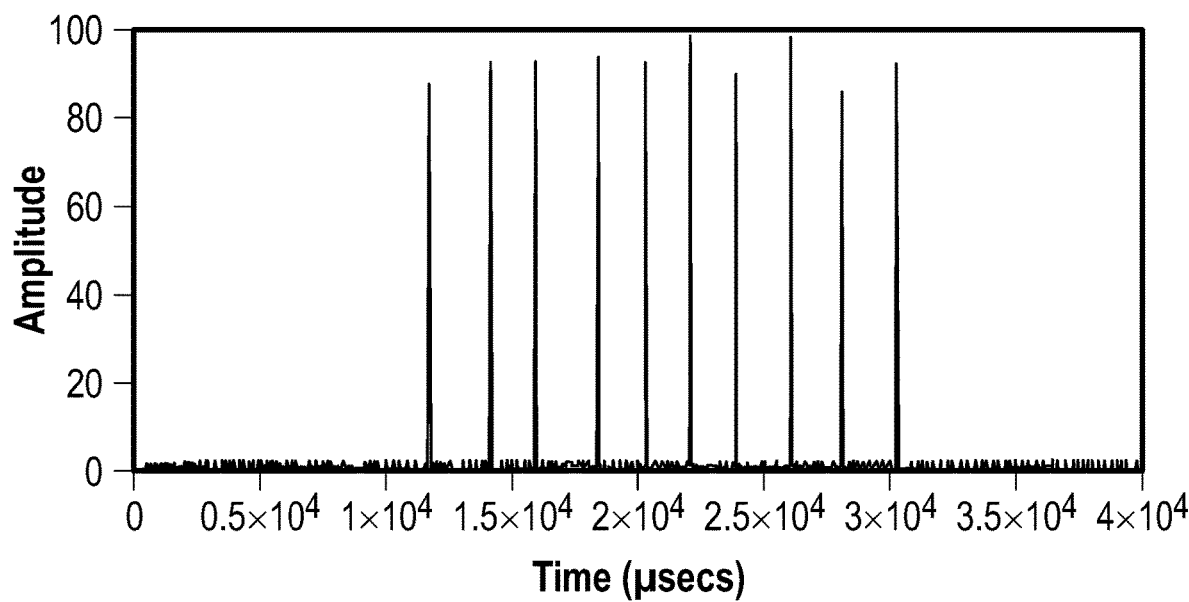
FIG. 2A depicts a possible pulse "burst" of an embodiment of an RF transmitter.

FIG. 2A depicts an embodiment of a burst from one tag of this example. During pulse interval modulation, the tag was idle for most of the time, except when the tag needed to transmit its pulses, which was less than 0.2% of the time with the design of this example.

Since there were two tags in the room of this example, the receiver adopted an algorithm to separate the signals from the tags, which could also tolerate some low level of collision. A "collision" occurred when the pluses from two tags overlapped in time.

Figure 2B:
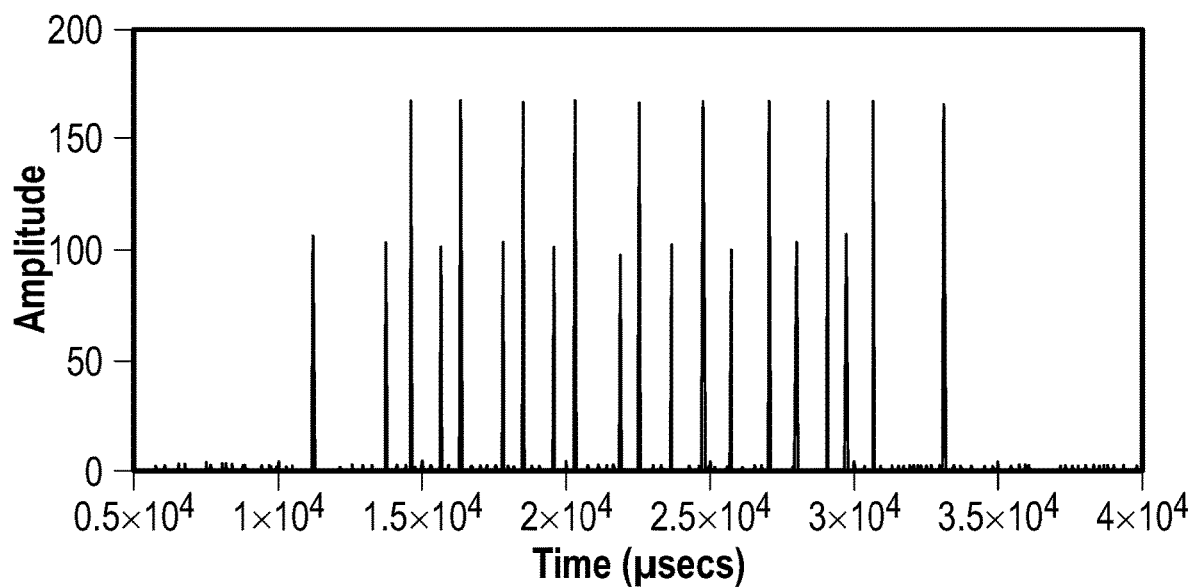
FIG. 2B depicts the possible pulse "bursts" of embodiments of two RF transmitters.

For example, FIG. 2B depicts the bursts from two tags of this example. In the current example, as the number of tags in the system was not large and the tag signatures were known to the receiver, a simple algorithm was used. The receiver scanned for pulses, and if it detected a first pulse, the pulse was assumed to be the first pulse of the burst of a tag. The tag was identified only if a matching condition was found, i.e., at least 9 pulses were found at the time the tag was supposed to send pulses according to its signature. The algorithm performed a linear scan on all tags, and outputted any tag that had the matching condition. A further check was adopted based on a particular aspect of the tag signature used in the current example. Basically, the first and the last pulse of a burst was separated by a constant time; therefore, a pulse could be the first pulse of a burst only if there also existed a pulse at the time of the last pulse of the burst. This check reduced the number of scans significantly.

Extracting the Wireless Channel Condition:

With pulse interval modulation, the condition of the wireless channel from a tag to a receiver of this example could be easily learned from the amplitude of the pulses. It was found that the measured amplitude was stationary when there was no human movement; however, with human movement, which changed the electromagnetic field, the measured amplitude showed significant variations.

Figure 3:
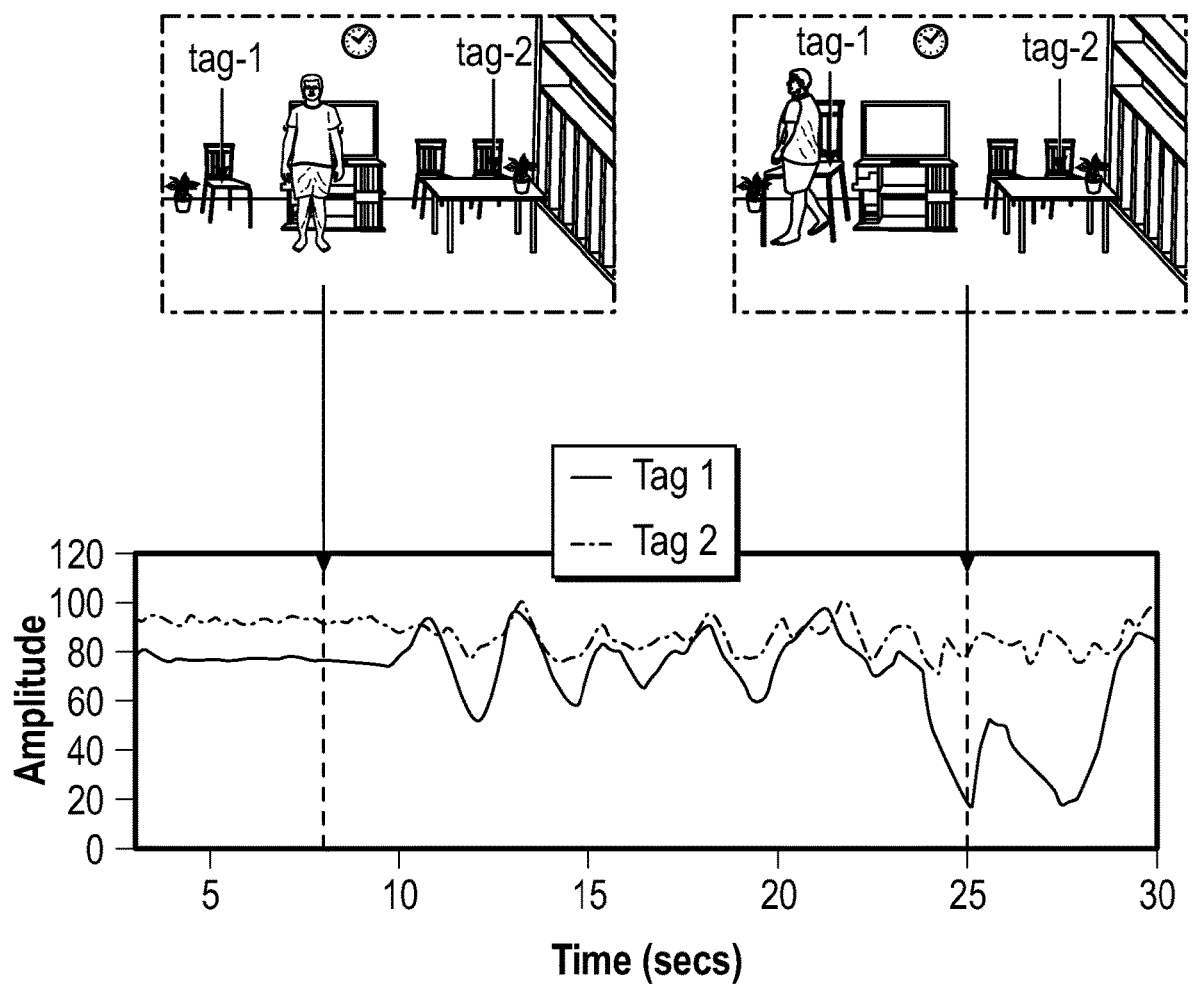
FIG. 3 depicts the amplitude of signals detected from embodiments of two RF transmitters during a human movement.

Therefore, the device of this example used the amplitude of the pulses as the decision variable to estimate whether or not the human test subject was moving. An example is depicted at FIG. 3, in which the amplitude of 2 tags are shown. The human was stationary up to 10 seconds, and started moving afterwards; correspondingly, the tags' signals were stationary in the first 10 seconds and started to fluctuate in various ways afterwards.

To produce a decision regarding whether the human was stationary or moving, the device calculated the standard deviation of the pulse amplitudes, and determined that a human movement had occurred if the standard deviation was more than 3 times the standard deviation of the signal when the human was not present. As a receiver may receive the signal from multiple tags, the tag with the largest fluctuation was used. This was because the purpose of the MD module was to detect any motion, and a motion existed if fluctuation could be detected in any channel.

It should be noted that the device of this example did not attempt to interpret the change of the wireless channel, i.e., to guess the type of activities that led to certain patterns of the observed signal. Instead, the device of this example used the existence or absence of the fluctuation of the signal to determine whether the human was moving or stationary, which was a simpler question and, therefore, could be answered with much higher accuracy.

The RF-base motion detection was more sensitive to movements near the tag or the receiver. After a fall near the tag or the receiver, the human test subject made some small movements. The tags of this example, however, were mounted at a certain height above the floor, and therefore were a certain distance away from the human after the falls because the human was on the floor. Further testing was conducted to uncover the response of the system to small human movements at 25 cm from the receiver, and this testing showed that micro movements made by a human after a fall did not affect the receiver enough to falsely classify the human as in motion. It was also discovered that human movement in other rooms did not cause significant changes to the signal, at least in part because the fluctuation was too small to cause any error.

Heat Sensing (HS) Module:

The Heat Sensing (HS) module was used by the device of this example to help determine whether or not the human was standing, and to estimate the distance of the human to the device. One or both of these determinations played a role in deciding which vibration threshold values could be used.

The HS module of this example was implemented with an Adafruit AMG8833 IR Thermal Camera due, at least in part, to its low cost. The thermal camera had 64 pixels, each having a spanning angle of about 7.5 degrees.

With correctly oriented upward viewing angles, the heat sensor of this example did not detect the human if the human was on the floor. The distance between the heat sensor and a human could be estimated, because the closer a human was to the heat sensor, the number of pixels reported high values increased.

This feature was demonstrated by heat maps corresponding to different distances between the heat sensor of this example and a human. A simple algorithm was adopted for estimating the distance. The algorithm first classified the pixels as high or low by comparing the reading to a preselected threshold, then the algorithm used the fraction of high pixels as the decision variable to determine the distance. In other words, the threshold was determined by data collected during the calibration time, during which no human was supposed to be near the sensor. For each pixel, the mean plus 4 times the standard deviation in the calibration data was used as the threshold. Based on the empirical data of this example, when the fraction of high pixels over the total number of pixels was at least 0.03, 0.25, or 0.5, the estimated results were within the room, 1 meter, or half meter, respectively. In other words, a human was "within the room" or 1 meter of a half a meter from the heat sensor.

The heat sensor was also used to determine whether a person was standing, by checking the existence of high pixels in the upper part of the sensor, based on the logic that a fallen or sitting human on the floor should not be detected in the upper part of the view, especially when the heat sensor was oriented in an upward direction as it was in this example.

Specifically, if the last known location of the human was within 0.5 m of the sensor, the top 50% of the view was used; for all other distances, the top 75% was used. The person was considered not standing if the fraction of high pixels in the considered area was less than 0.03. Sometimes, due to noise, the heat sensor detected some high pixels in its top portion, even when the human was not in the view, leading it to falsely detect a human. To overcome this, a metric based on the average distance between the high pixels was used in this example, as the distance between individual high pixels, in case of noise, was random, whereas for a human, they would have been closely packed, thereby resulting in a smaller value. A relatively loose threshold was selected for this example to eliminate the possibility that a fallen person was considered standing.

It should be noted that the foregoing algorithm could also address cases in which a heat source is present in the environment. Heat sources, such as a fireplace or a cup containing hot water or other beverage, when present in the surrounding environment, may be detected by one or more pixels of a heat sensor, and those one or more pixels may be confused with those detecting a body temperature. During the testing described herein, it was found that relatively smaller heat sources, such as a cup of hot water or other beverage, when place at distances farther than 1 m from a device, were significantly smaller than the typical areas mapped to a single pixel, and, therefore, usually did not register a temperature significantly higher than ambient room temperature.

When placed near a heat sensor, relatively larger heat sources, such as a fireplace or a large pot of a hot liquid, typically had outer edges having a lower temperature than their middle portions, and, therefore, sometimes were detected as "human pixels". When placed farther away from a device, however, the decay in infrared signal strength caused the sensor to register a temperature that was lower than the actual temperature of the heat source, but were still sometimes classified as "human pixels."

To overcome this, an algorithm was devised to remove non-human heat source pixels before running the distance and standing estimation modules, based on the fact that most heat sources resulted in "hot pixels", i.e., pixels detecting temperatures that exceed a human's body temperature. The algorithm first checked if any pixel exceeded an upper human body temperature threshold. If such pixels were found, then the algorithm discarded them, as well as any adjacent pixels, which may also have been affected by the heat source. The higher the temperature reading, the more adjacent pixels were removed. In one implementation, if a pixel had a reading of more than 40, then pixels with a distance of 3 or less were removed; otherwise, pixels with a distance of 2 were removed. After some pixels were removed, the bottom row of pixels typically needed to detect whether a human was standing were redefined as the lowest pixel that was not removed in each column of an inspected area. If more than 50% of the pixels were estimated to detect a non-human heat source, the heat sensor data could be ignored, and such a situation was treated, at least in some instances, the same as when the human was not in view of the heat sensor.

The preselected values used for the human body temperature threshold were also calibrated by the system. To establish the lower threshold, a clustering algorithm was used to cluster the sensor readings into two clusters. The cluster with the lower values was assumed to be the ambient temperature, and the lower threshold was the mean temperature of this cluster plus 8 times the standard deviation of all temperature readings in this cluster. The upper threshold was calibrated only once per sensor, by recording the maximum temperature reported by the heat sensor pixels when the human was standing close to the sensor and remained constant thereafter. Although the human body temperature detected by a heat sensor may be lower if the human wears multiple layers of clothing, this usually occurs only in colder temperatures when the overall ambient temperature of the room is lower, so it should still be higher than the lower threshold. The heat sensor was calibrated at regular intervals as long as no movement was detected in the room, i.e., the human was present in the room, but not mobile.

Floor Vibration Detection (FVD) Module:

The Floor Vibration Detection (FVD) module of this example reported the vibration of the floor.

This detection was an important part of the device of this example, because most, if not all falls, including the tested falls, should introduce a certain level of vibration to the floor. The FVD module of this example was implemented with RaspberryShake, a seismograph device for Raspberry Pi, which constantly reported a vibration reading every 20 ms. The vibration reading reflected the amount of vibration detected by the sensor.

Typically, the maximum observed vibration reading reflected the intensity of the vibration, and was therefore used by the device of this example as the decision variable. The vibration reading was compared with certain threshold values to help determine if a fall had occurred.

Even when the same human or the same object falls in the same manner, many factors could impact, and possibly change, the reading, including the distance of the human or object to the sensor, the floor type (i.e., concrete or wood), etc. Therefore, the threshold values were learned in this example. The learning was achieved by a simple process.

During installation of the system, simulated falling events were created in the room at a number of calibration locations to record the signal amplitude to determine the threshold value, i.e., the vibration amplitude was recorded for falls at 0.5 m, 1 m, and 3 m away from the device. For example, the vibration threshold was 32821, 18867, and 14882, in the living room test in the examples herein.

Example 2—Device Output

In this example, one person walked into the room that included the device of Example 1, dropped a 10 pound object about 1 meter from the device, walked away, and then fell on the floor about 2 meters from the device.

Figure 4:
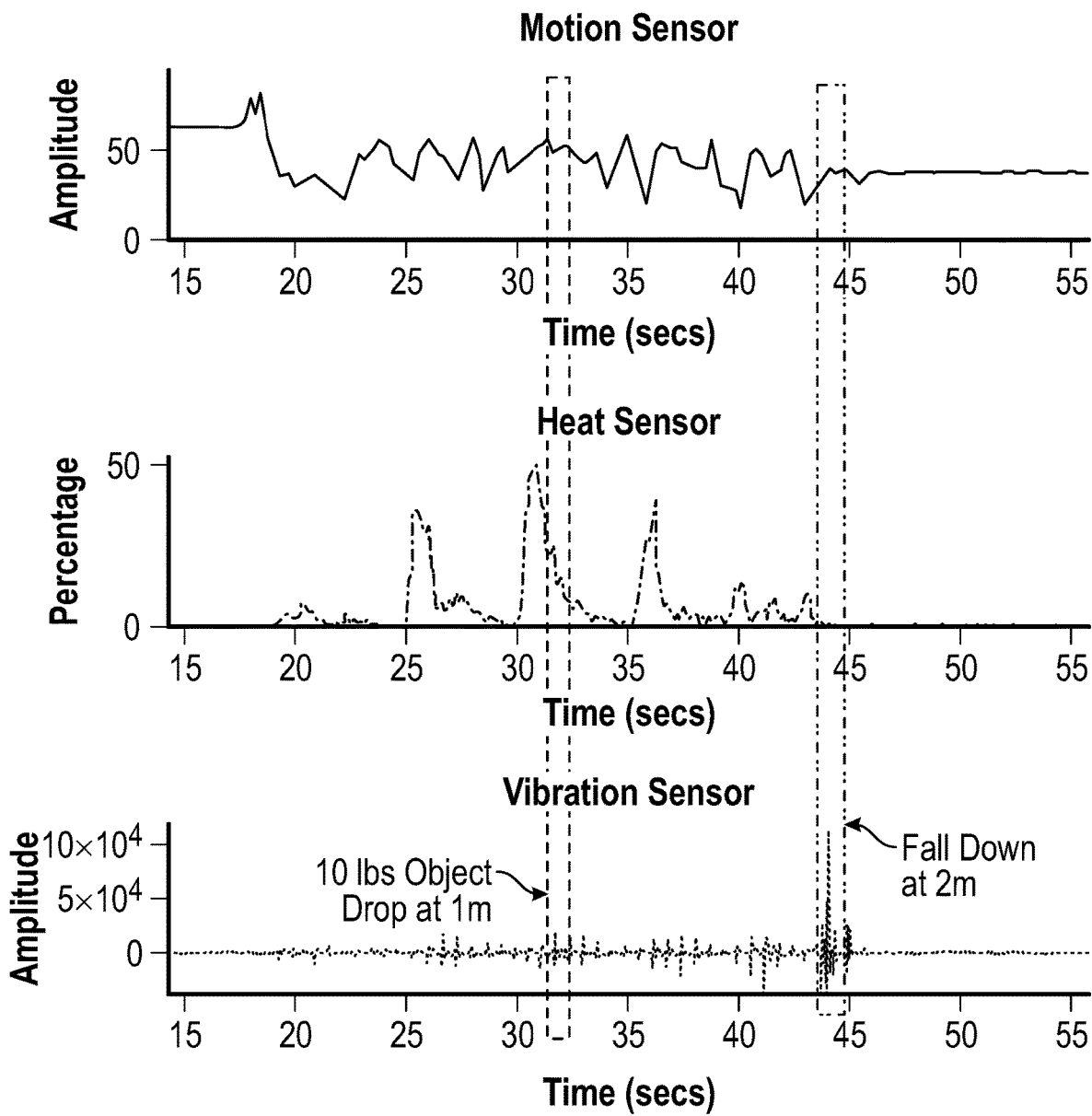
FIG. 4 depicts the output of an embodiment of a system before, during, and after the dropping of a ten pound weight and a fall of a human.

The responses of the sensors of the device to these events are depicted at FIG. 4.

As depicted in the motion sensor reading of FIG. 4, the fall resulted in some changes to the signal, and the changes were followed by a relatively stationary period. The relatively stationary period was believed to result from the fact that the fall action changed the electromagnetic field, thereby resulting in changed signals. After the fall, when the human was on the floor, stationary signals were observed.

Therefore, a changing signal followed by a stationary period, currently set as 5 seconds, was referred to as the motion-to-stationary transition in this example. Such a transition may also occur as a result of other activities, such as a human leaving the room of Example 1.

As depicted at FIG. 4, the heat sensor outputted low readings after the human fell, likely because the human was lying on the floor and out of the view of the top half of the heat sensor. The heat sensor reading also was higher when the human was closer to the sensor. Therefore, the heat sensor output was used to estimate the distance between the human and the device.

In the vibration sensor reading of FIG. 4, the amplitude of the fall was much larger than the amplitude caused by the walking steps of the human and the object drop, even when the object was dropped at distances relatively closer to the device.

Example 3—Fall Detection Algorithm

In this example, two fall detection algorithms were designed for use with the system of Example 1.
First Algorithm:
The first algorithm of this example may be parsed as follows:

| Algorithm 1 MultiSense Fall Detection Algorithm |  |
| --- | --- |
| 1: | if the motion sensor detects a motion-to-stationary transition then |
| 2: | if the vibration reading is larger than a threshold based on the estimated distance then |
| 3: | if the heat sensor does not detect the human to be standing after the transition then |
| 4: | Declare a Fall |
| 5: | else |
| 6: | Declare Fall if no movement is detected by the motion sensor in the next 30 seconds |
| 7: | end if |
| 8: | end if |
| 9: | end if |

The first detection algorithm of this example constantly checked the motion sensor for the motion-to-stationary transition, a feature of falls. Once such a transition was detected, the algorithm estimated the distance of the human to the device with the heat sensor data. Currently, the possible distances were: within 0.5 m, within 1 m, in the room, or not in the view.

The distance was used to select a threshold for the vibration data; higher thresholds were used for smaller distances. If the vibration reading was higher than the selected threshold and the heat sensor did not detect the human after the transition, the algorithm declared a fall. Otherwise, if the heat sensor still detected a standing human after the transition, the algorithm waited for 30 seconds, and still declared a fall is no movement was detected in the 30 seconds. This was because if it was an actual fall, the heat sensor likely detected some heat source and not an actual human. However, after the fall, the human would likely have been stationary and therefore the algorithm could still detect the fall. If it was not a fall but some activity such as jumping or stomping, it was extremely unlikely that the human remained stationary for 30 seconds.

Second Algorithm:
The second algorithm of this example may be parsed as follows:

| Algorithm 2 Fall Detection Algorithm |  |
| --- | --- |
| 1: | If the motion sensor detects a motion-to-stationary transition then |
| 2: | query the heat sensor to obtain the distance estimator ε before the transition |
| 3: | if the heat sensor does not detect the human to be standing, based on ε, after the transition then |
| 4: | Declare Fall if the vibration reading is larger than a threshold based on ε |
| 5: | end if |
| 6: | end if |

The second detection algorithm of this example constantly checked the motion sensor for the motion-to-stationary transition, a feature of falls. Once such a transition was detected, the algorithm checked the heat sensor before and after the transition.

Using the data from before the transition, the detection algorithm estimated the distance of the human from the sensor, which is referred to herein as ε. ε had four possibilities: within 0.5 m, within 1 m, in the room, or not in the view.

Based on this estimation, the detection algorithm used a heuristic to determine if the human was standing after the transition. If the heat sensor did not detect a standing human at this point (which is a typical feature of a fall event), then a fall was declared if the vibration sensor reading during the transition period was higher than a threshold selected according to the distance of the human to the device before the transition, as estimated by the heat sensor data.

The estimated distance had 4 possibilities: within 0.5 m of the device, within 1 m of the device, in the room, or not in the view, and a higher threshold was used for the smaller distances. If the heat sensor did not detect the human before and after the transition, a fall was still declared if the vibration reading was higher than a threshold selected based on E. The thresholds used were determined during a calibration phase. During calibration, each threshold was substantially the recorded vibration value collected when a soft fall occurred at specific locations.

The relative simplicity of the fall detection algorithm of this example made it possible to conduct an analysis of the system's performance. The analysis was performed by measuring the False Negative (FN) and False Positive (FP) ratios, which corresponded to cases in which an actual fall was not detected, and in which a non-fall activity was declared incorrectly as a fall, respectively. It should be noted that the device of this example was designed for use by senior citizens living alone; therefore, in the interest of safety, any significant variation of the signal was assumed to be due to the human.

False Negative:

From the algorithm, it was clear that a fall would be detected if 1) the fall generated the motion-to-stationary transition, 2) the human was not detected as standing by the heat sensor after the transition, and 3) the fall generated vibrations of sufficient amplitude.

Such conditions should likely be true for all types of falls. Therefore, the device of this example had very low False Negative ratios. Correct system parameters and threshold values were used to detect events such as the motion-to-stationary transition.

False Positive:

The False Positive analysis was conducted to test the performance of the device, because many types of activities may occur in a daily setting. Therefore, the analysis of this example focused on establishing a list of conditions that an activity must meet to cause a FP event. Assuming no object falls on its own, the conditions were as follows:

Condition 1.

The human must have been moving in the room before the detected motion-to-stationary transition, and then kept still until after the detected transition. This condition reflected the fact that the fluctuation of the RF signal before the transition could only be caused by a moving human in the room. The stationary RF signal after the transition could be caused by the inactivity of the same human still in the room, or by the human leaving the room. The latter, however, would not lead to any floor vibration level higher than the threshold.

Condition 2.

The human was either always out of the view of the heat sensor, or was blocked by some object after the transition, as the human did not fall and therefore not on the floor. This is consistent with the foregoing algorithm of this example.

Condition 3.

At the detected motion-to-stationary transition, the human must have taken some action that caused the vibration sensor to register a high value; further, such action could not have resulted from the dropping of any normal object. This condition reflected the fact that if the human was within 1 m of the device, as the heat sensor should have had a clear view within 1 m, it should detect the human before the transition, and the device of this example, therefore, used the correct vibration threshold, which was higher than the vibration caused by the falling of the object. Otherwise, in the worst case, if the human was not in the view of the heat sensor, the device of this example used the lowermost threshold. It was found that even for an object of 20 pounds, the vibration reading at over 1 m was lower than the conservative threshold.

Therefore, it was concluded that an FP event could only be caused by some human action which caused high motion and vibration readings, but such action could not be the dropping of an object; in addition, after the action, if the human kept still, and somehow managed to stay away from the view of the heat sensor. Such activities, however, should be very rare, as indicated by the experimental evaluations herein.

Example 4—False Negative Evaluations

False Negative tests of the system of Example 1 were conducted in rooms resembling a typical living room and bathroom. The system tested in this example included one RF tag, as opposed to two RF tags as depicted at FIG. 1. Otherwise, the systems were identical, and the system of this example was arranged in the manner explained in the following paragraph.

The RF tag used in the motion sensor of this example was placed at about 1 meter above the floor, and the heat sensor of this example was placed on the ground and pointing upwards at an angle of about 60 degrees. In each testing environment, the test subject was initially outside the room for over 5 seconds in order to achieve the calibration needed by the motion and the heat sensor. The vibration sensor was calibrated for each environment by performing very soft falls. For the living room, the falls started at the corner of the room that was opposite from the device, then at a distance of 1 meter, and finally at a distance of 0.5 m. As the bathroom was relatively small, the calibration fall was performed only at one distance.

A. Living Room Tests

A total of 100 experiments were conducted inside the living room of this example, which included carpet on a concrete floor. The living room of this example had a size of about 16 square meters.

In each experiment, after the 5-second calibration period, the test object started some normal activity, such as walking, and then simulated a fall at a random time. The evaluation included different kinds of falls, including hard falls, soft falls, forward falls, and backward falls, which occurred at various distances from the device.

It was found that the device of this example detected all falls. In the following sections, the results are organized according to the view of the heat sensor, and the signal from a typical example is shown for each case to illustrate why the device of this example detected the falls successfully.

Within the View of the Heat Sensor:

In 53% of the living room tests, the fall occurred where the heat sensor could determine that the person was seen somewhere in the room before the fall at a distance over 1 m from the device, but not after the fall.

Figure 5:
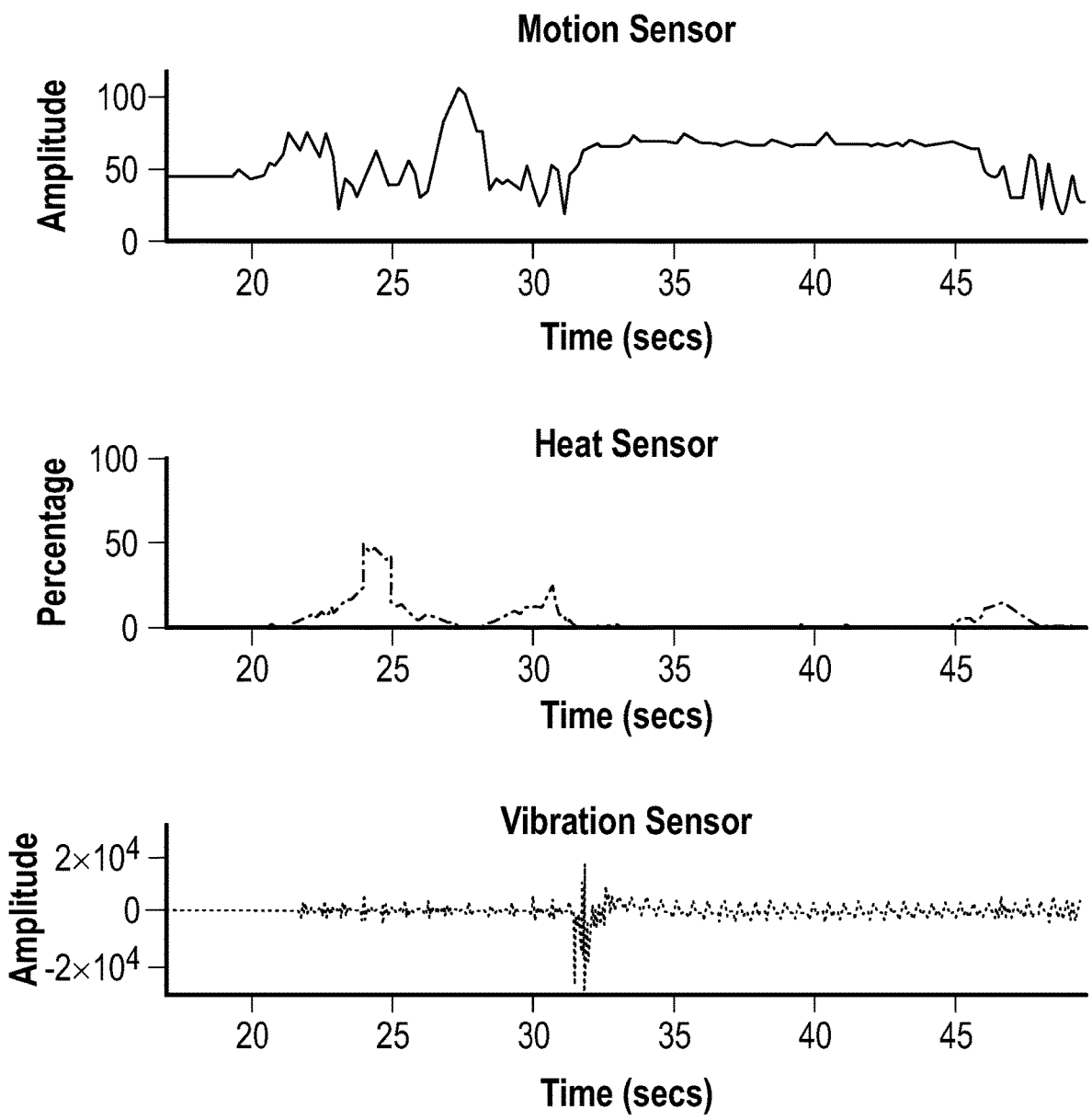
FIG. 5 depicts the output of an embodiment of a system, including the output before, during, and after a fall of a human.

This category of tests covered the most common areas where a person could fall down inside the room. A typical case depicted at FIG. 5, which shows the data outputted by a fall inside the view of the heat sensor. The fall of FIG. 5 occurred at about 32 seconds. During the fall, both the motion sensor and the vibration sensor registered large fluctuation or readings. After the fall, the motion sensor reading stopped fluctuating, and the heat sensor output was close to zero, thereby meeting the criteria of the device of this example to declare a fall.

Figure 6:
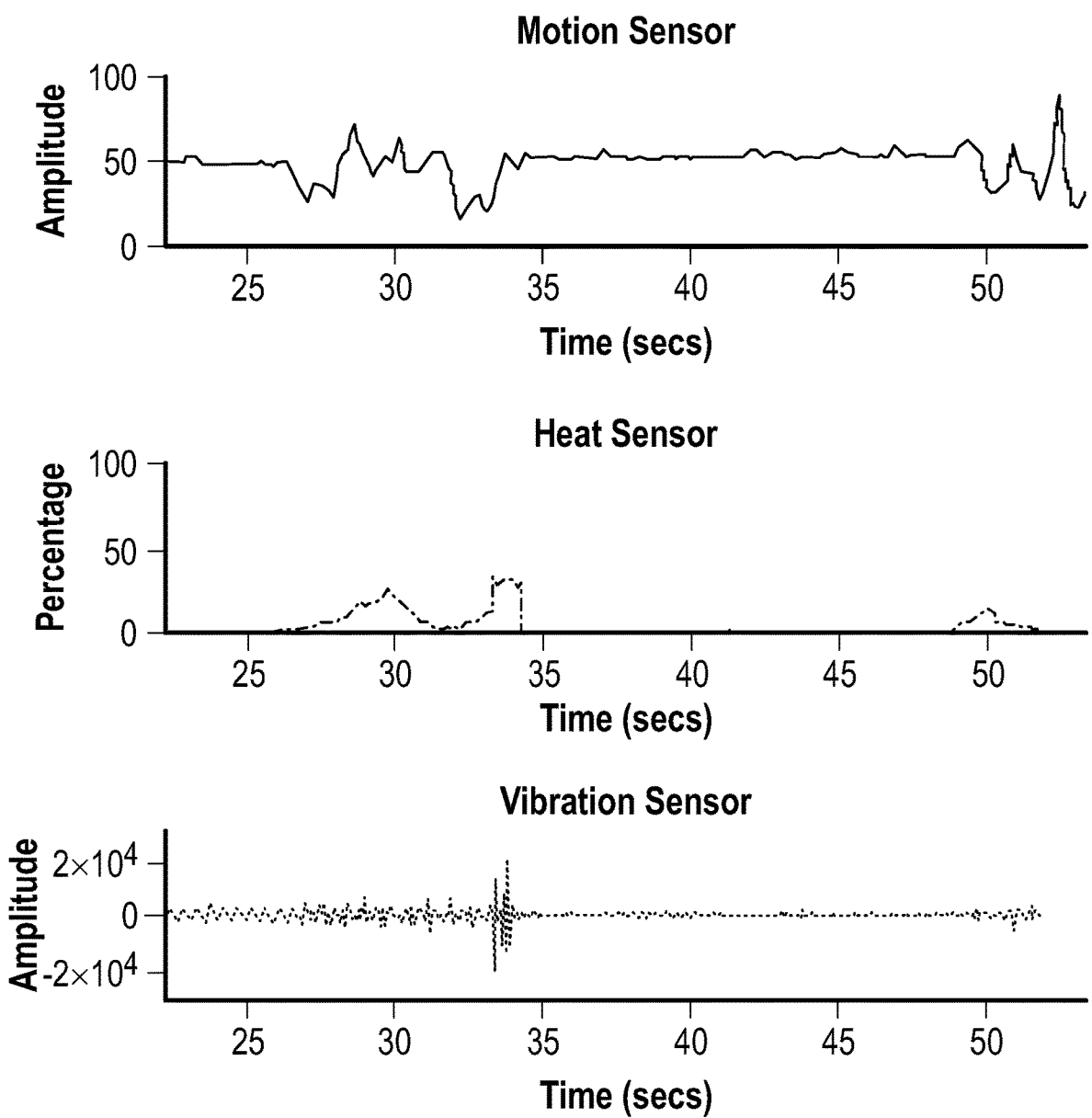
FIG. 6 depicts the output of an embodiment of a system, including the output before, during, and after a fall of a human.

Within a Meter to the Heat Sensor:

In 36% of the living room tests, a fall was simulated at a distance of about 1 meter from the sensor. The data of FIG. 6 shows that just before the motion-to-stationary transition at about 34 seconds, the test subject occupied more than 25% of the high pixels in the heat sensor. As a result, a higher vibration threshold was applied, which was still exceeded due to the fact that a real human fall occurred.

Figure 7:
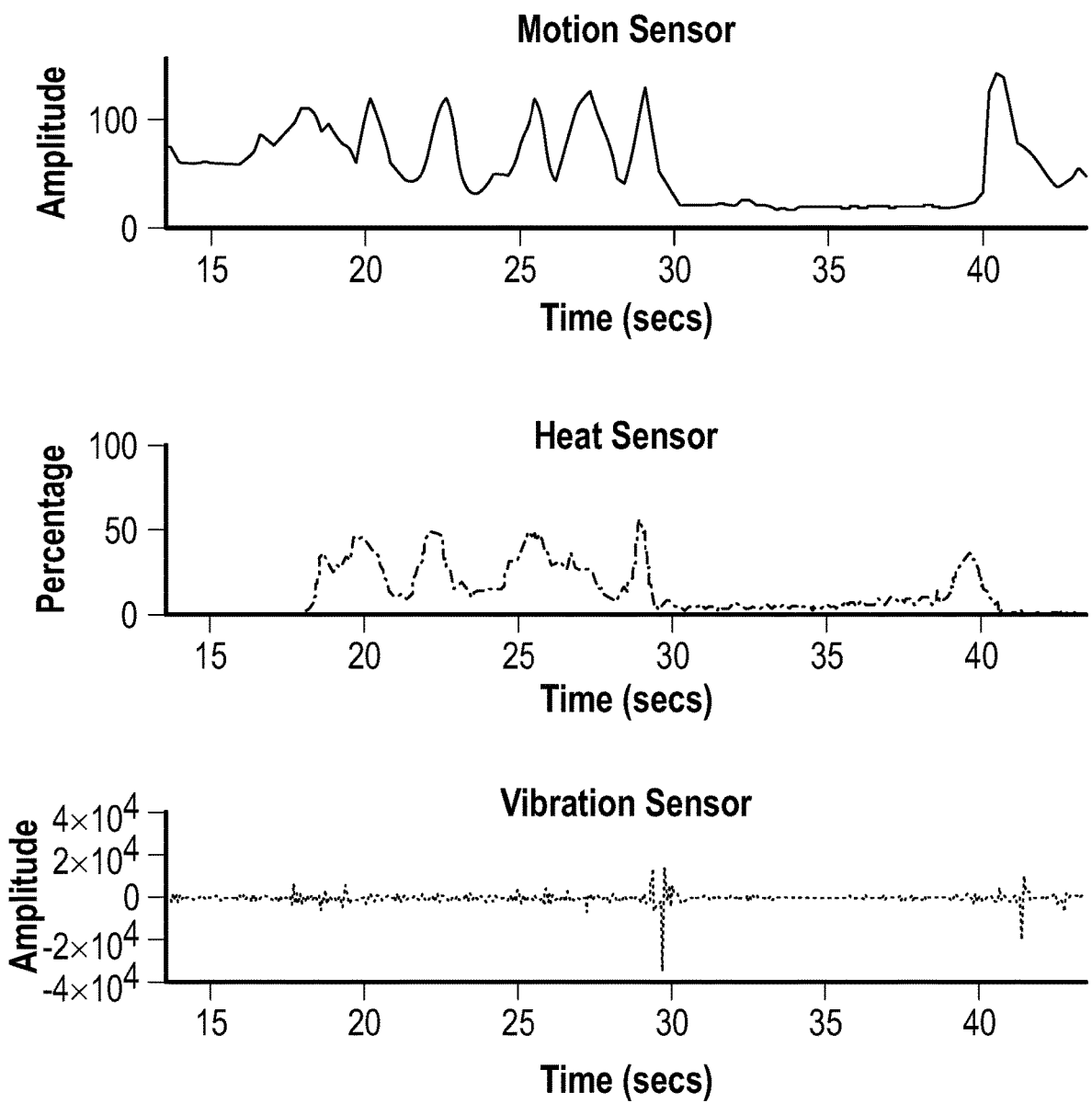
FIG. 7 depicts the output of an embodiment of a system, including the output before, during, and after a fall of a human.

Within Half a Meter Distance to the Heat Sensor:

In 1% of the living room tests, the fall was simulated within 0.5 meters from the sensors. As depicted at FIG. 7, the percentage of high pixels in the heat sensor was more than 50% just before the fall at about 30 seconds, after which the vibration sensor registered a value larger than the vibration threshold at 0.5 m, and the human was not visible in the top half of the heat sensor.

Outside the View of the Heat Sensor:

About 10% of the living room tests were conducted so that the fall occurred at a location where the heat sensor could not detect the person before and after the fall.

Figure 8:
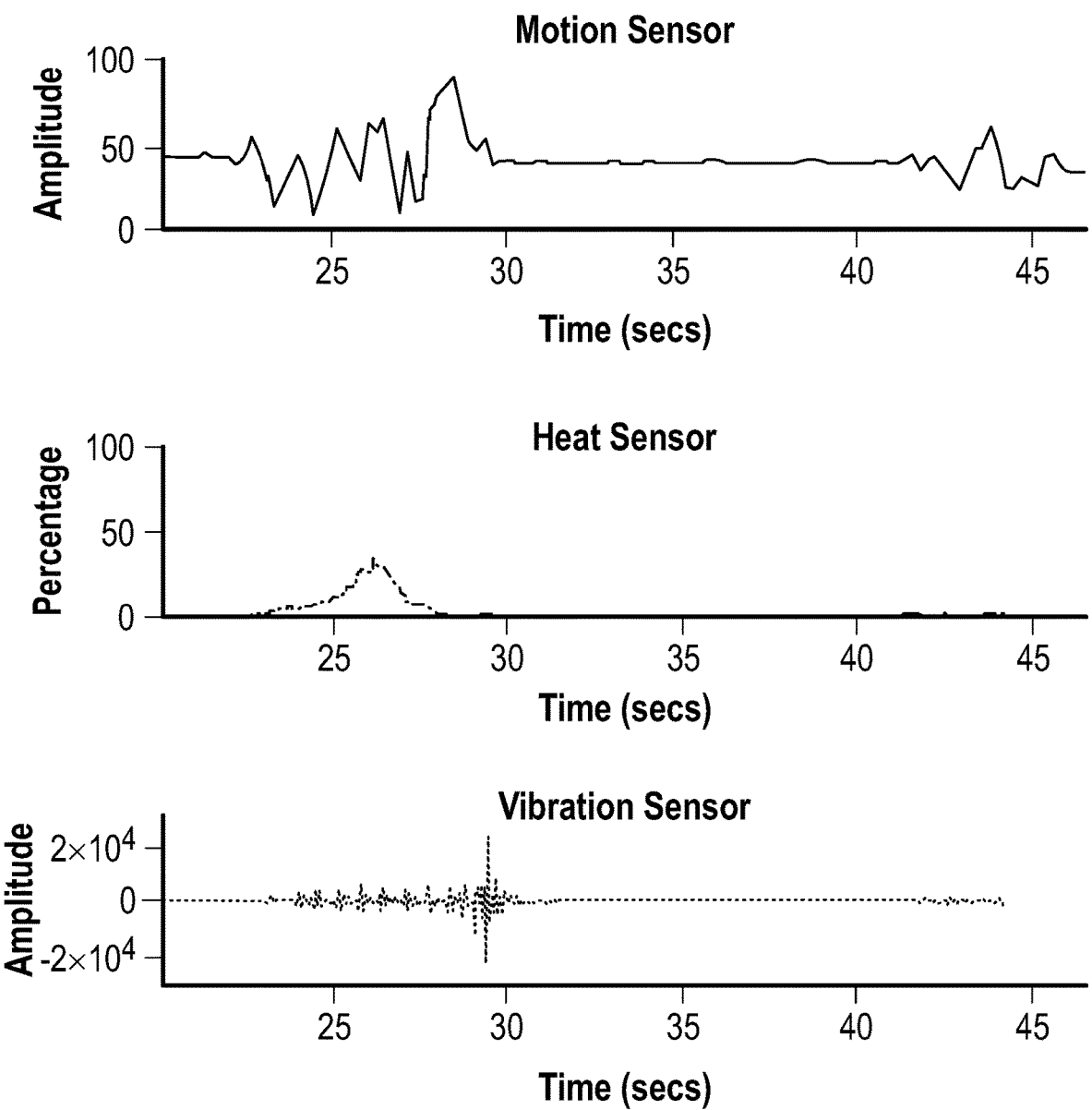
FIG. 8 depicts the output of an embodiment of a system, including the output before, during, and after a fall of a human.

As depicted at FIG. 8, the heat sensor could detect the person until about 27 seconds, after which the person moved out of the view of the heat sensor. This can occur if there are blind spots in the room where the heat sensor cannot detect a human, or if the person falls behind an object, such as a piece of furniture, which blocks the view of the heat sensor. With proper placement and orientation, these types of blind areas can be minimized.

Still, the device of this example determined that an actual fall occurred (at about 29 seconds) by applying the lowest vibration threshold when the device detected a transition on the motion sensor, and the lowest vibration threshold was exceeded because an actual human fall occurred.

B. Bathroom Tests

A total of 50 experiments were conducted inside a room resembling a typical bathroom. Falls were simulated inside a bathtub, and the sensors were located outside the bathtub. As with the living room tests, in each experiment, the calibration period was followed by some normal activity of the test subject, such as getting into the bathtub, and then the test subject fell inside the bathtub.

As the size of the bathroom of this example was relatively small, a single vibration threshold of 22034 was applied. Two types of scenarios were considered. The first scenario was with the shower curtains open, which represented situations in which a person falls while getting into or out of the bathtub. The second scenario was with the shower curtains drawn or closed, which represented situations in which the person slips and falls while taking a shower. It was found that the device of this example detected all falls in both scenarios.

Figure 9:
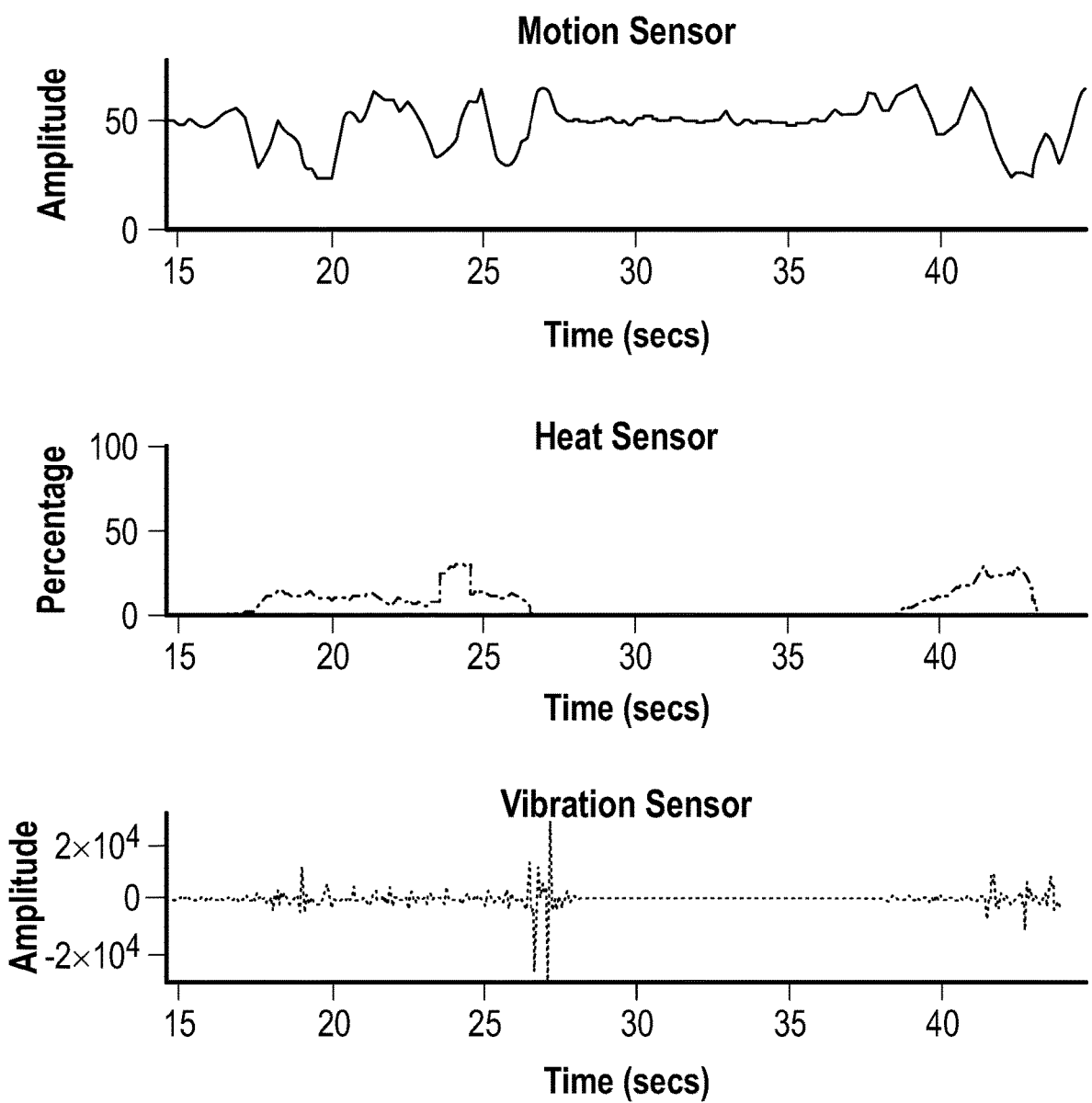
FIG. 9 depicts the output of an embodiment of a system, including the output before, during, and after a fall of a human.

With the Shower Curtains Open:

This test was conducted in 50% of the cases. A typical example of the system output collected during these tests is depicted at FIG. 9.

With the shower curtains open, the heat sensor could pick up, i.e., "see", the human. The fall was detected because a motion-to-stationary transition occurred at about 27 seconds, followed by the person being undetected on the heat sensor, and the vibration sensor detected a relatively large vibration at the time of transition.

With the Shower Curtains Drawn:

In the remaining 50% of the cases, falls were simulated with the shower curtains drawn. The heat sensor, as a result, could not determine the position of the person. However, this scenario did not pose a problem for the device of this example, because it made determinations based on the data from the motion and vibration sensors. These tests were similar to those conducted in the living room of this example when the person was outside the view of the heat sensor.

Figure 10:
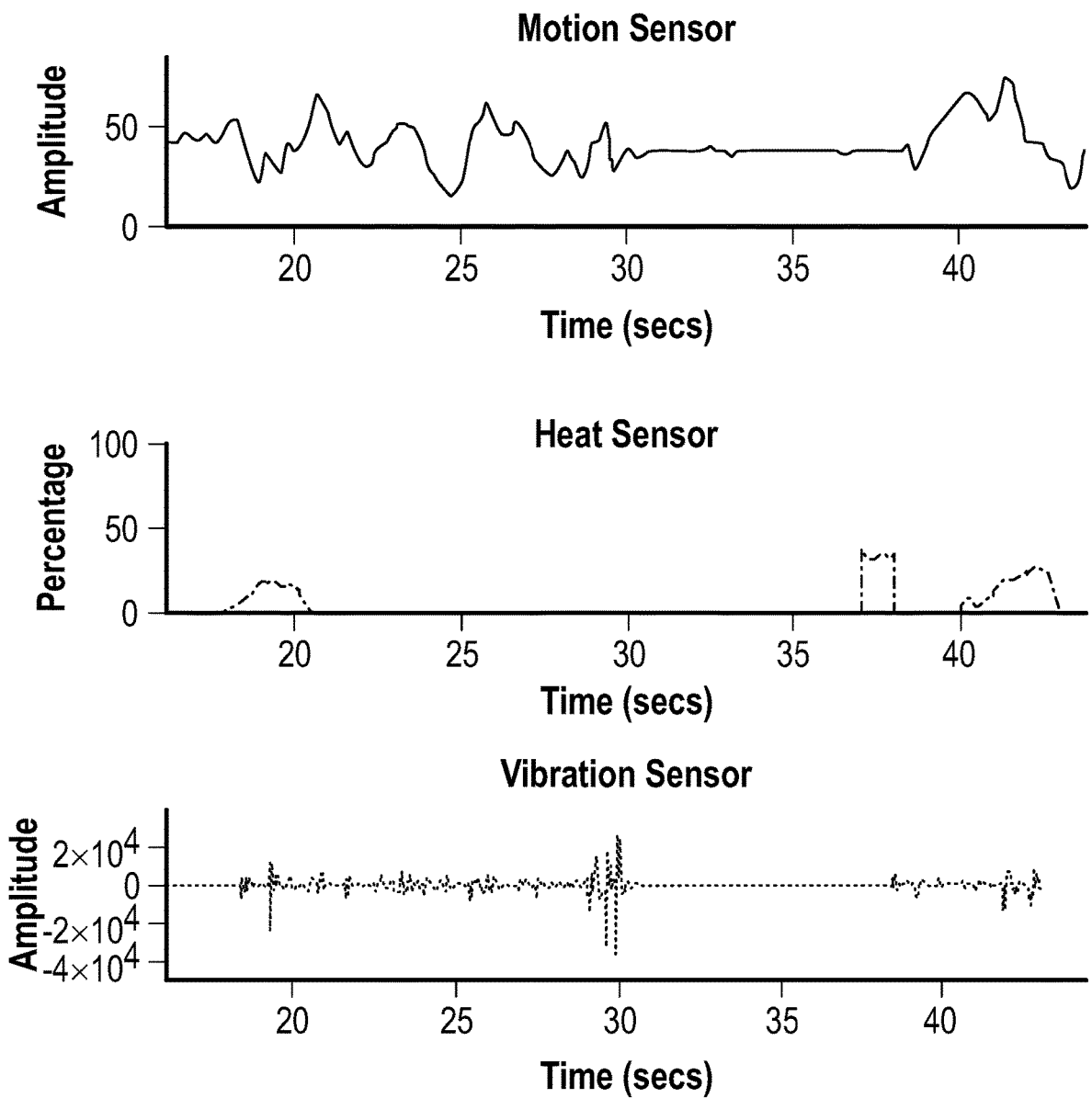
FIG. 10 depicts the output of an embodiment of a system, including the output before, during, and after a fall of a human.

A typical example of the system output collected during these tests is depicted at FIG. 10, where the fall occurred at 30 seconds. This may have increased the chances of a False Positive in the bathroom; however, most of the activities that appeared to lead to False Positives were unlikely to occur in the bathroom. Even for activities that might occur, such as door slams, standing up, or sitting down, none of these activities registered anything significant on the vibration sensor.

Example 5—False Positive Daily Use Test

The devices of Example 4 that employed the first algorithm and the second algorithm were also tested over a 24-hour period in a living room and produced 0 False Negatives and 0 False Positives per hour. Specifically, during the test period, 7 human falls were simulated at random times, and the device of this example detected all falls correctly. In addition, usual day-to-day activities, such as leaving or entering the room, sitting down, standing up, walking around, etc., were conducted, and the device of this example did not report any falls for such activities.

Example 6—False Positive Stress Tests

Stress tests were designed to test the device of Example 4 that employed the second algorithm with activities that were not falls, such as jumping in various ways. The activities were selected to challenge the accuracy of the fall detection system. The tests were done in the same living room as the False Negative tests. Each type of activity was repeated 5 times and in various ways.

The device of this example did not incorrectly declare any falls, except for two types of activities, namely a "Freeze Jump" and a "Stomp Far Away". These two activities, however, are unlikely to be unintentionally performed by seniors. In the following sections, each type of activity is discussed, along with the signal of one typical case.

A. Freeze Jumping at Close Distances

Figure 11:
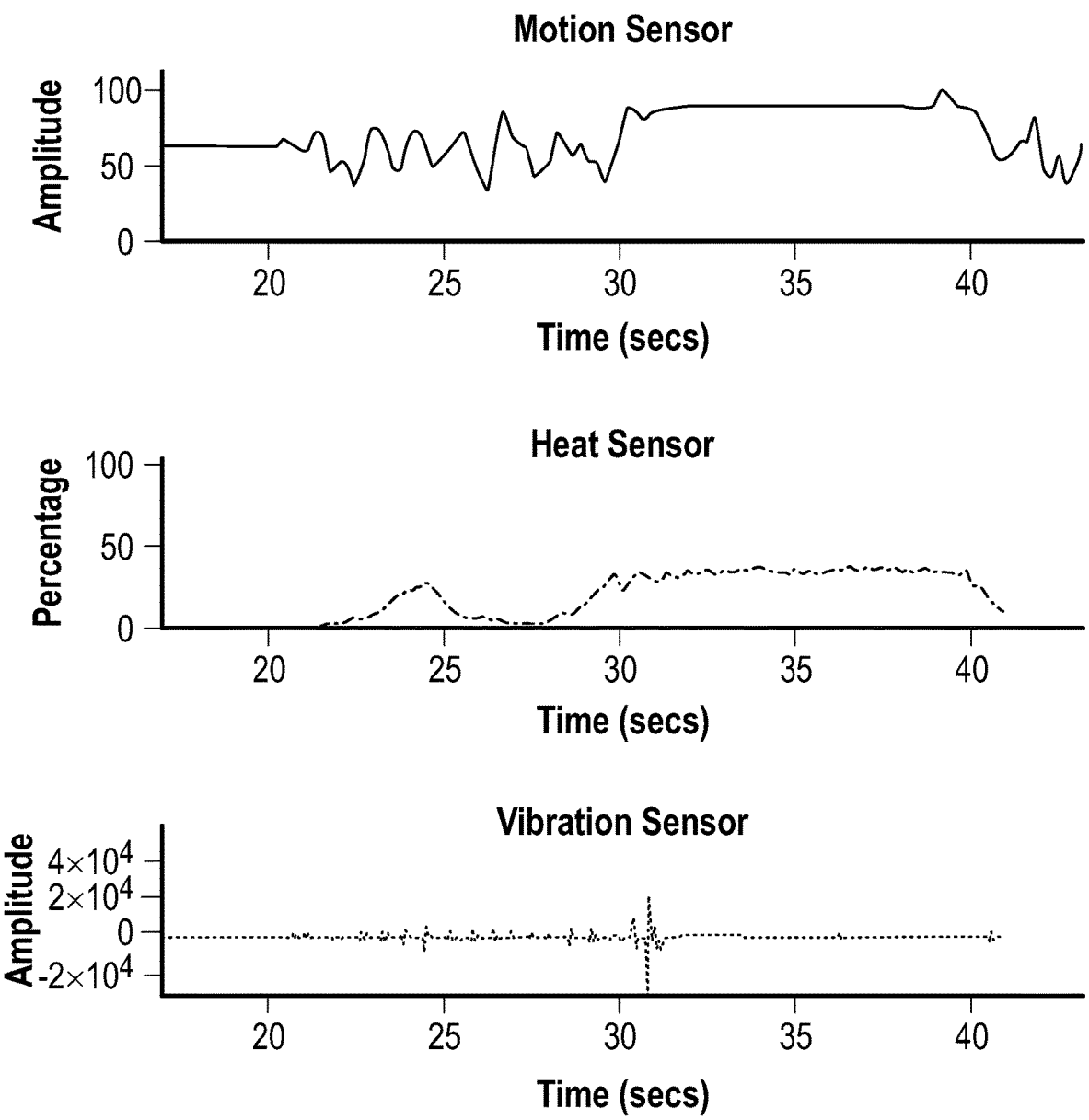
FIG. 11 depicts the output of an embodiment of a system, including the output before, during, and after a fall of a human.

This test represented a scenario in which a person was initially walking, then jumped at a location close to the device, and stood still. The device of this example did not consider this activity a fall because although a motion-to-stationary transition occurred, and the vibration sensor likely registered a large vibration value, the heat sensor still detected the human, as shown at FIG. 11.

B. Freeze Stomping at Close Distances

This scenario was very similar to freeze jumping at close distances, and the device of this example used a similar logic to avoid declaring the activity a fall.

C. Normal Jumping

This test represented a scenario in which a person walking inside the room suddenly jumped, and then continued walking. Unlike the previous case in which the person freeze jumped or stomped near the device, the heat sensor may or may not be able to detect the person in the scenario of this section, especially if the person is not within the view of the heat sensor. Further, the vibration sensor may also register some large vibration values.

However, the device of this example still worked because the motion sensor did not register a stationary period after the jump, and therefore the device determined that the person was still in motion.

D. Normal Stomping

This scenario was again very similar to the normal jumping case, and for the same reason, the device of this example did not consider the "normal stomping" activity a fall.

E. Sitting Down and Standing Up

This test represented an everyday scenario in which a person enters the room, sits down for a while, gets up and leaves the room.

Although the motion sensor detected a motion-to-stationary transition when the person sat down, the device of this example easily determined, in multiple ways, that this activity was not a fall.

For example, if the person was still in the view of the heat sensor after sitting down, a fall was not declared. For the testing of this example, the worst possible scenario was used, which occurred when the person sat down in a place where the heat sensor was blocked.

Figure 12:
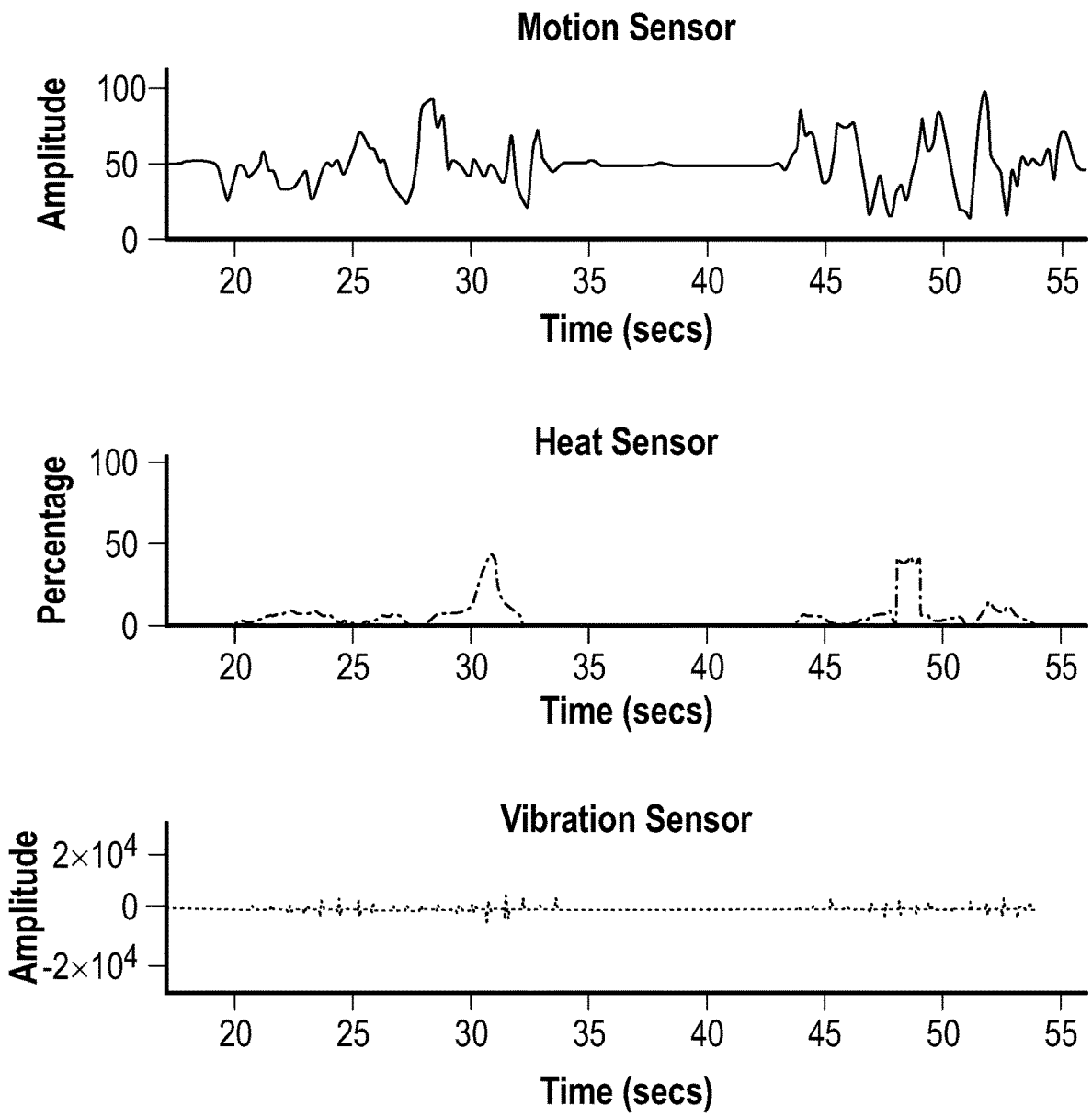
FIG. 12 depicts the output of an embodiment of a system, including the output before, during, and after a fall of a human.

For example, as depicted at FIG. 12, after sitting down at about 32 seconds, the heat sensor did not pick up the person. However, sitting down and/or standing up did not result in large vibrations, therefore the device of this example determined that a fall did not occur.

F. Walking and then Standing

This test represented an everyday scenario in which a person entered the room, walked around, and then suddenly stopped moving and stood at a spot.

This was equivalent to an activity in which a person walked around the room and then left the room. In both cases, a motion-to-stationary transition was detected. If the person was in the view of the heat sensor when the walking stopped, the heat sensor detected the person and no fall was declared. Even if the person was not detected as standing by the heat sensor, such as when leaving the room, the vibration data was not large enough to declare a fall.

G. Slamming a Door

This test represented an everyday scenario in which a person enters a room, walks around and then slams the door upon exiting the room. In some sense, this was very similar to the previous scenario that included walking and suddenly standing, as the device of this example used the lack of a large vibration to determine that no fall occurred.

It should be noted that while a door slam may cause vibrations, the vibrations from a door slam pass primarily along the walls of the room. The vibration sensor of the device, therefore, does not detect these vibrations, at least in part because the vibration sensor is placed on the floor and out of contact with the wall.

In one test, the person slammed the door at about 31 seconds, but the vibration sensor did not register anything significant to indicate a fall.

H. Normal Object Drop

This test represented an everyday scenario in which a person inside a room dropped an object while walking, stopped to pick it up, and then continued walking.

There are multiple ways the device of this example worked correctly in this case. Whether the heat sensor detected the person or not, and/or whether the vibration caused by the object was larger than the threshold, the motion sensor determined that the person was not stationary and therefore no fall was declared.

I. Freeze Object Drop

This test represented a scenario in which a person inside a room dropped an object while walking, and then stopped walking. In the test, a heavy object weighing 20 pounds was dropped at various distances from the device.

Figure 13:
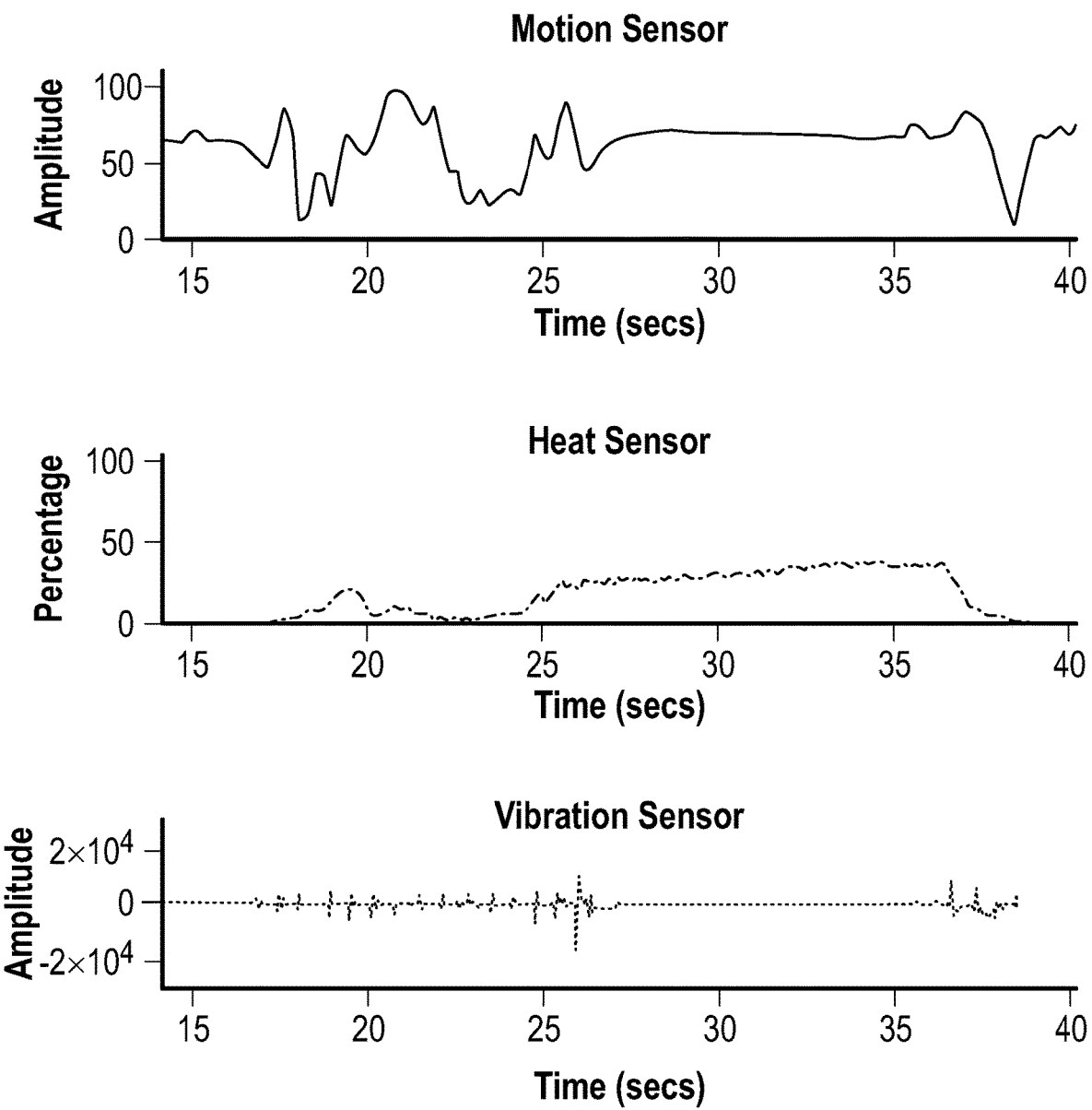
FIG. 13 depicts the output of an embodiment of a system, including the output before, during, and after a fall of a human.

As shown at FIG. 13, when the drop occurred within 1 meter of the device, and the person could be detected by the heat sensor after the drop, the device of this example did not consider it a fall, even when the vibration sensor picked up a large vibration at 26 seconds, just before the motion-to-stationary transition.

If, for some reason, the person stepped outside the coverage of the heat sensor during the drop or an object blocked the view of the heat sensor after the drop, the device of this example applied a high vibration threshold, because the last known location of the person was within 1 meter of the device, and the heat sensor should have a clear view. In the evaluation, it was found that even 20 pound objects did not cause a vibration as large as a human fall at the same distance.

Figure 14:
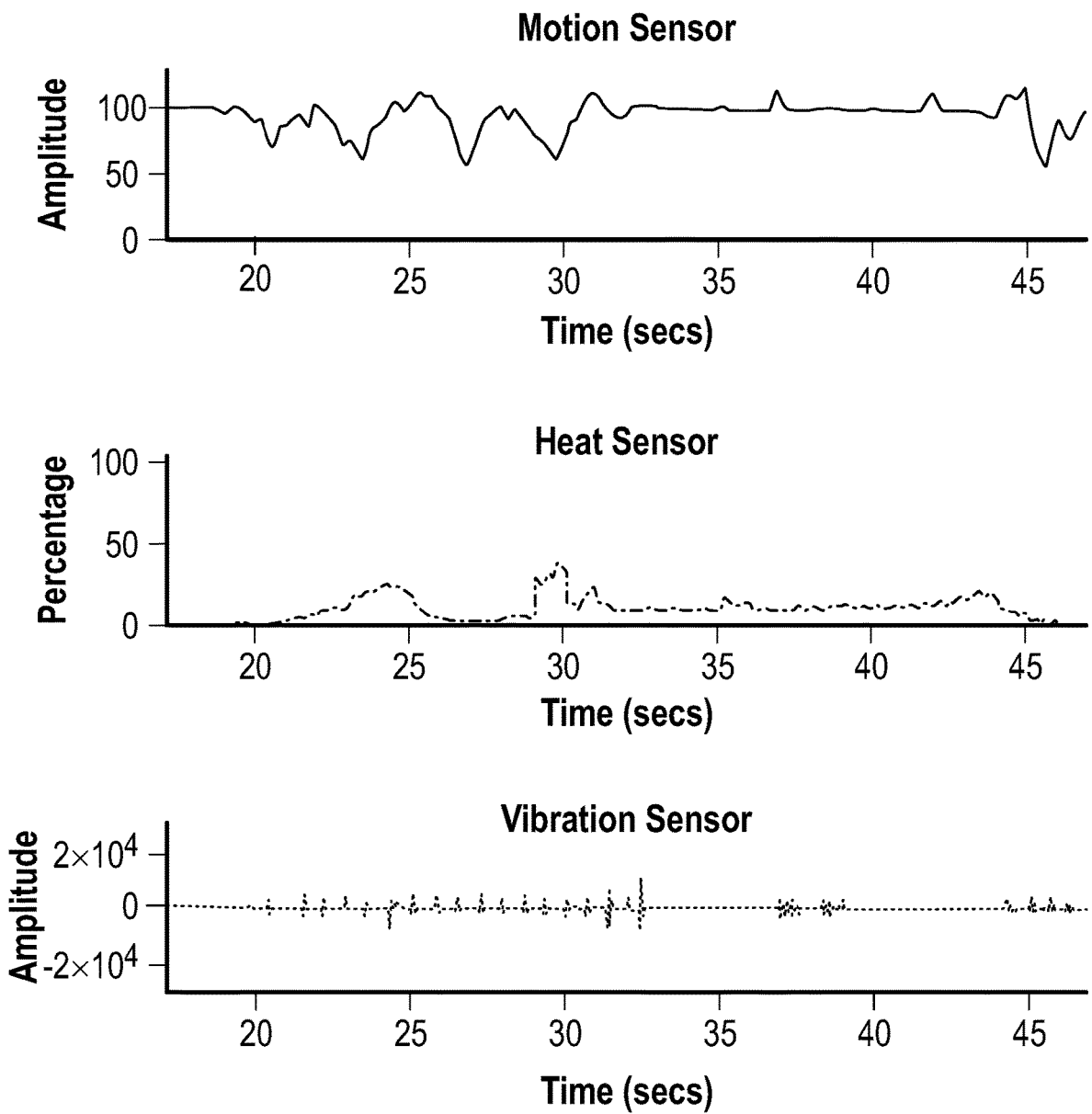
FIG. 14 depicts the output of an embodiment of a system, including the output before, during, and after a fall of a human.

Similarly, if the object was dropped at a distance greater than 1 meter from the device, the device of this example did not consider it a fall because the person was either still in the view of the heat sensor, such as in FIG. 14, after the object drop at 33 seconds; or the registered vibration was lower than the threshold.

J. Freeze Jumping Far Away

This test represented a scenario in which a person was initially walking, then jumped at a location far away from the heat sensor, and then stood still.

This was a scenario in which the motion sensor detected a transition, the heat sensor did not detect the person, and the vibration sensor likely registered a large vibration value.

Figure 15:
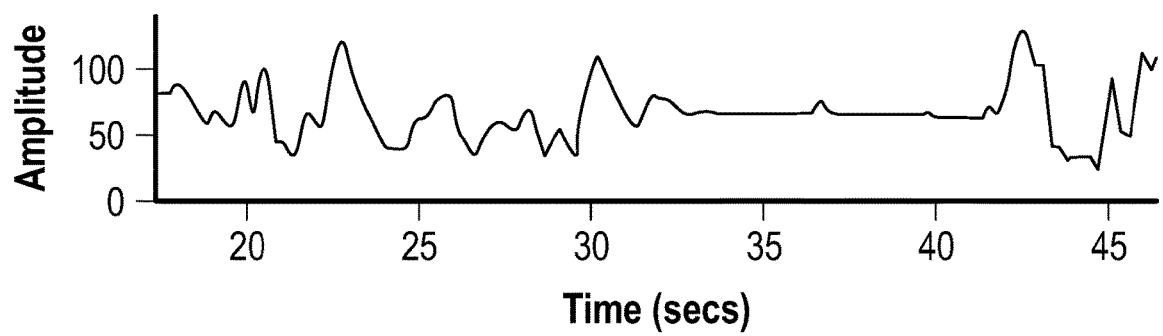
FIG. 15 depicts the output of an embodiment of a system, including the output before, during, and after a fall of a human.
Figure 15:
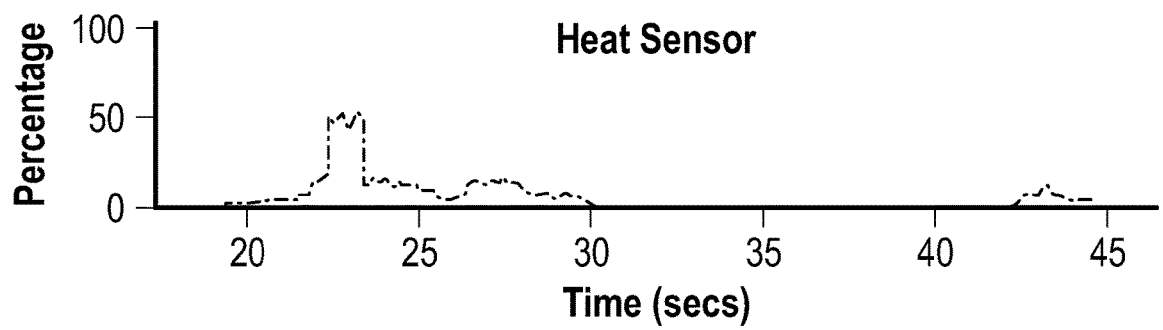
Figure 15:
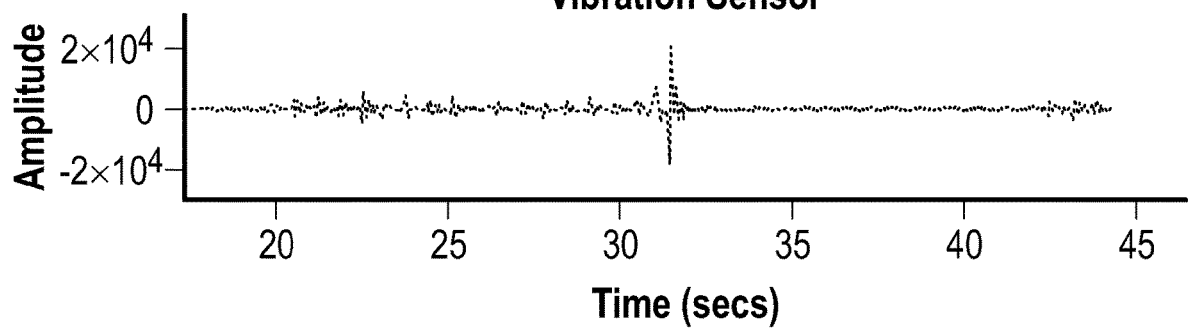

An example is depicted at FIG. 15, where the jump occurred at 32 seconds. The device of this example applied the smallest vibration threshold, and registered a False Positive error in this case, as vibrations caused by a jump are comparable to those caused by a human fall. However, this type of activity is exceptional and is typically not a part of the everyday activities of adults, particularly senior adults.

K. Freeze Stomping Far Away

Figure 16:
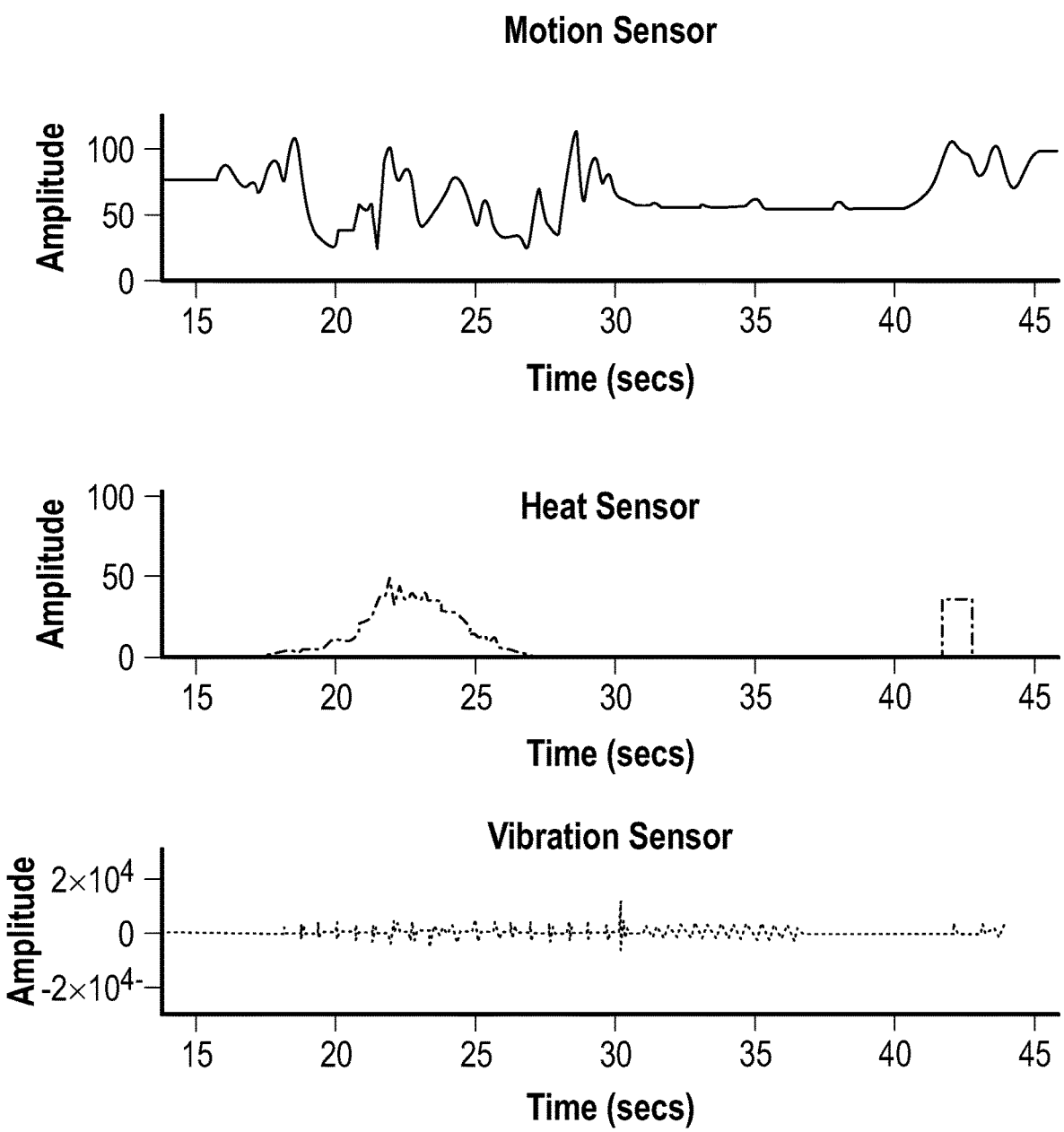
FIG. 16 depicts the output of an embodiment of a system, including the output before, during, and after a fall of a human.

This test represented a scenario where a person was initially walking, then stomped on the ground, and then stood still. It was very similar to the freeze jumping at far distances discussed herein, and an example of the test is depicted at FIG. 16. The device of this example may raise a False Positive for this type of activity as well. However, as the vibration caused by stomps are usually much lower than an actual human fall or an actual human jump, it was found that only 20% of such stomps resulted in False Positives.

Example 7—Comparative Testing

The following table depicts a comparison of the device of the foregoing examples and some existing wearable-free fall detection systems. The performance numbers are those reported in the literature where indicated, and the costs were estimated based on the cost of the sensors used in device of the foregoing examples.

| | Comparative Testing | | | | | |
|---|---|---|---|---|---|---|
| Name | False Negatives | False Positives | Cost | Privacy Issue | Relies on Training | Bathroom Test |
| Device of the foregoing Examples | 0% | 0% | $150 | No | No | Yes |
| Wang, Y. et al., "WiFall: Device-Free | 2% | 12% | $80 | No | Yes | No |

-continued

| | | Comparative Testing | | | | |
|---|---|---|---|---|---|---|
| Name | False Negatives | False Positives | Cost | Privacy Issue | Relies on Training | Bathroom Test |
| Fall Detection by Wireless Networks," IEEE Trans. Mob. Comput., 16(2): 581-594, 2017. | | | | | | |
| Skubic, M. et al., "Testing non-wearable fall detection methods in the homes of older adults," IEEE Conference of the Engineering in Medicine and Biology Society, August 2016. | 2% | 1 per month | $140 | Yes | Yes | No |
| Zigel, Y. et al., "A method for automatic fall detection of elderly people using floor vibrations and sound-proof of concept on human mimicking doll falls," IEEE Trans. on Biomedical Eng., 56(12): 2858-2867, 2009. | 3% | 1.4% | $60 | No | Yes | No |
| Li, Y. et al., "Efficient source separation algorithms for acoustic fall detection using a Microsoft Kinect," IEEE Trans. Biomed. Eng., 61(3): 745-755, 2014. | 2% | 0.4 per hour | $140 | No | No | No |
| Debard, G., "Camera-based fall detection using a particle filter," Proc. IEEE Eng. in Med. and Bio., 6947-6950, June 2015. | 24% | 59% | $200 | Yes | Yes | No |

The device of the foregoing examples exhibited generally superior performance, and was not susceptible to privacy breaches or the imperfections associated with the training data.

Example 8—Coping with Non-Fall Activities

Activities were designed to illustrate the internal logic of the device of Example 4 (that employed the first algorithm) with activities that were not falls. The activities were selected to challenge the accuracy of the fall detection system.

The device of this example did not incorrectly declare any falls, except for two types of activities, namely a "Freeze Jump" and a "Stomp Far Away". These two activities, however, are unlikely to be unintentionally performed by senior adults.

A. Everyday Activities

Figure 17:
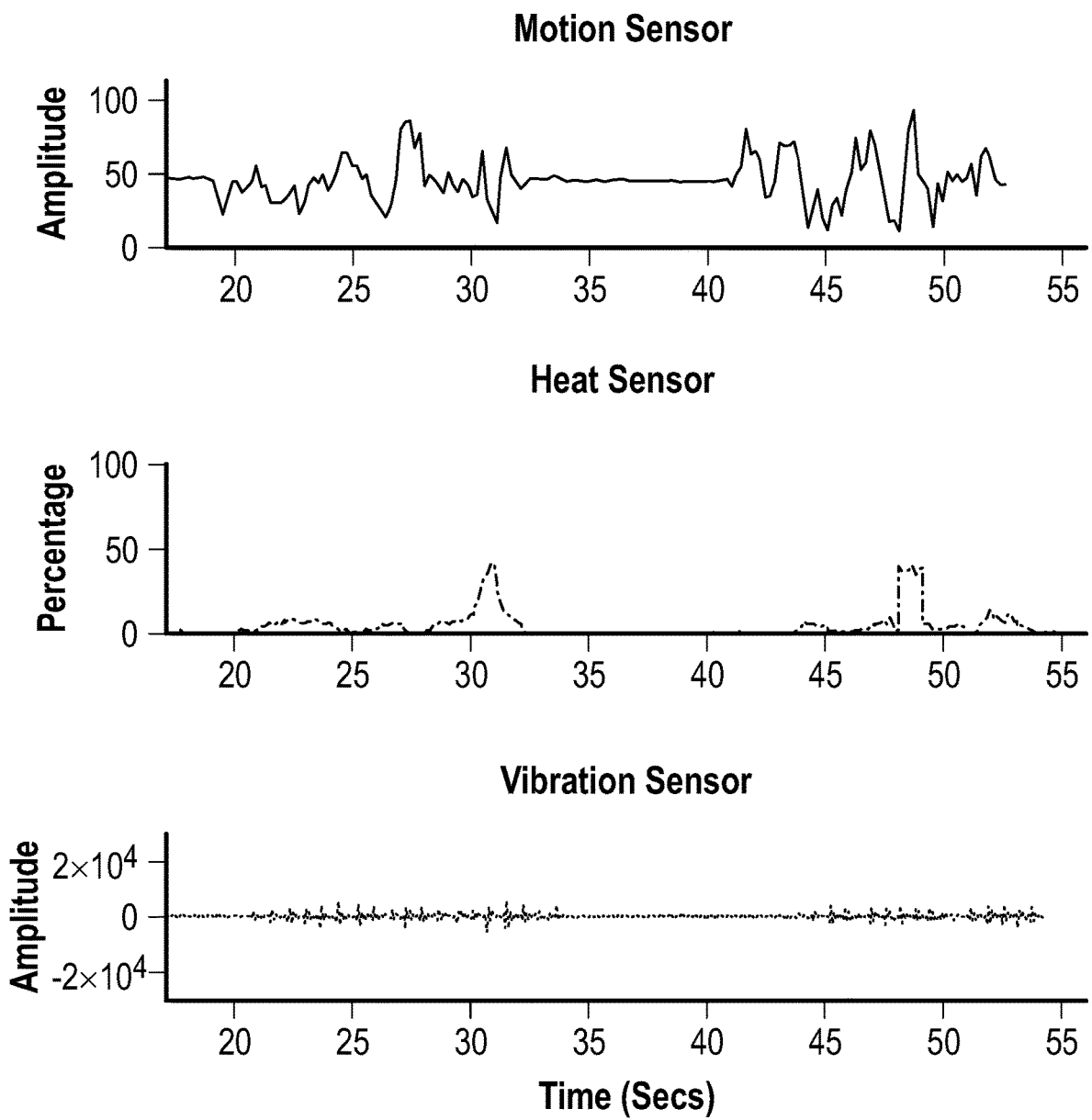
FIG. 17 depicts the output of an embodiment of a system, including the output before, during, and after a fall of a human.

Everyday activities included: entering a room, walking in the room, possibly stopping for a while in the middle, sitting down for a while, getting up, and leaving the room, possibly slamming the door on the way out. Even though the motion sensor may detect a motion-to-stationary transition, for example, when the person sat down, leaved the room, or made a stop during walking, and the heat sensor may even be blocked by the chair, the system easily determined no fall has occurred, because none of these activities generated vibrations that exceeded the vibration threshold. Even door slamming did not generate vibration readings that exceeded the threshold because the vibration was mainly on the walls, while the vibration sensor was on the floor. An example is seen in FIG. 17 where the person sat down in a place where the heat sensor was blocked.

B. Normal Object Drop

Figure 18:
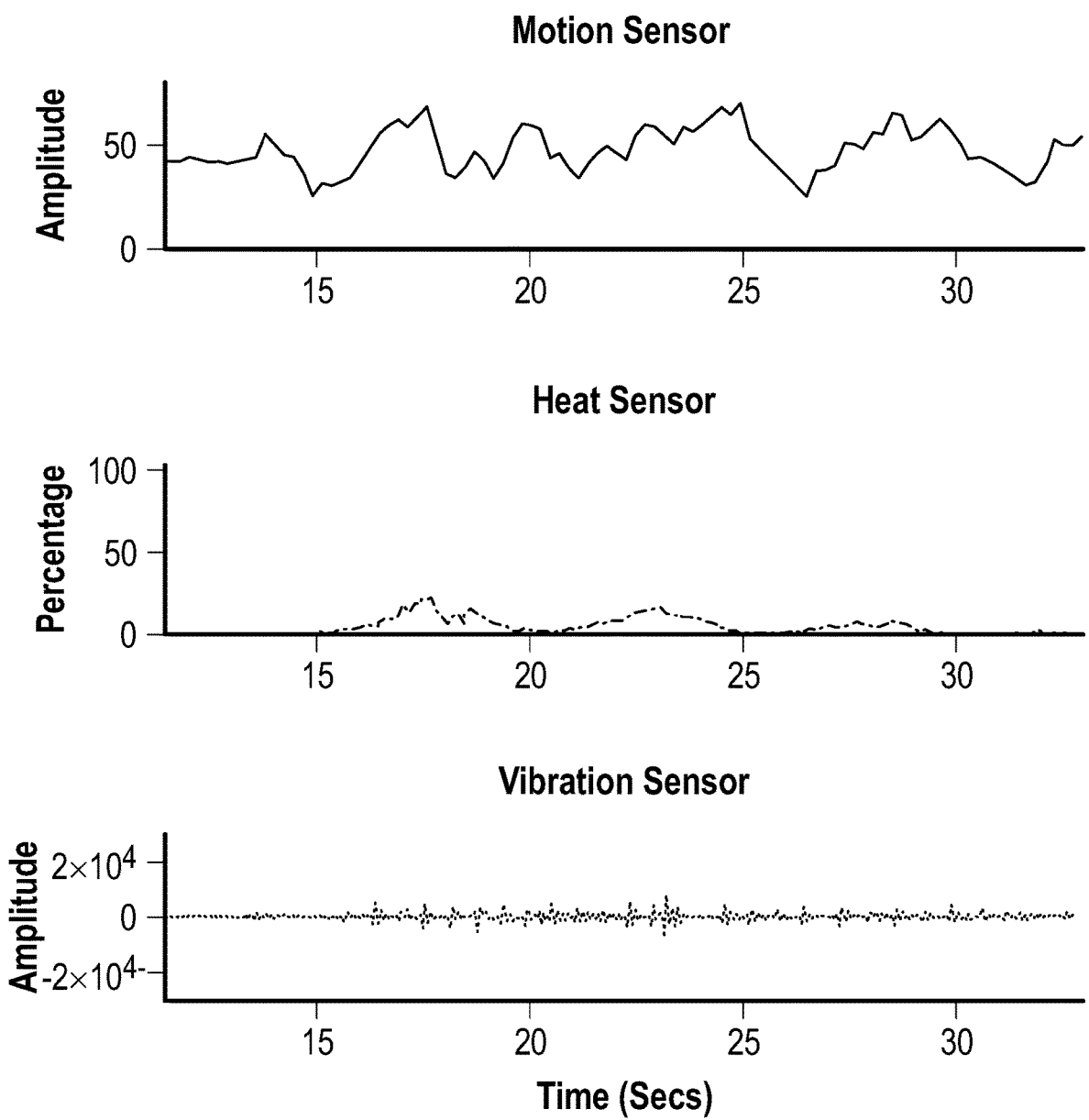
FIG. 18 depicts the output of an embodiment of a system, including the output before, during, and after a fall of a human.

It could happen that a person drops an object while walking, stops to pick it up, and then continues walking. There were multiple ways the system could work correctly in this case. Whether or not the heat sensor detected the person, and whether or not the vibration caused by the object was larger than the threshold, the motion sensor determined that the person was not stationary and therefore no fall was declared. FIG. 18 shows a scenario where a 20-pound object was dropped.

C. Freeze Object Drop

Figure 19:
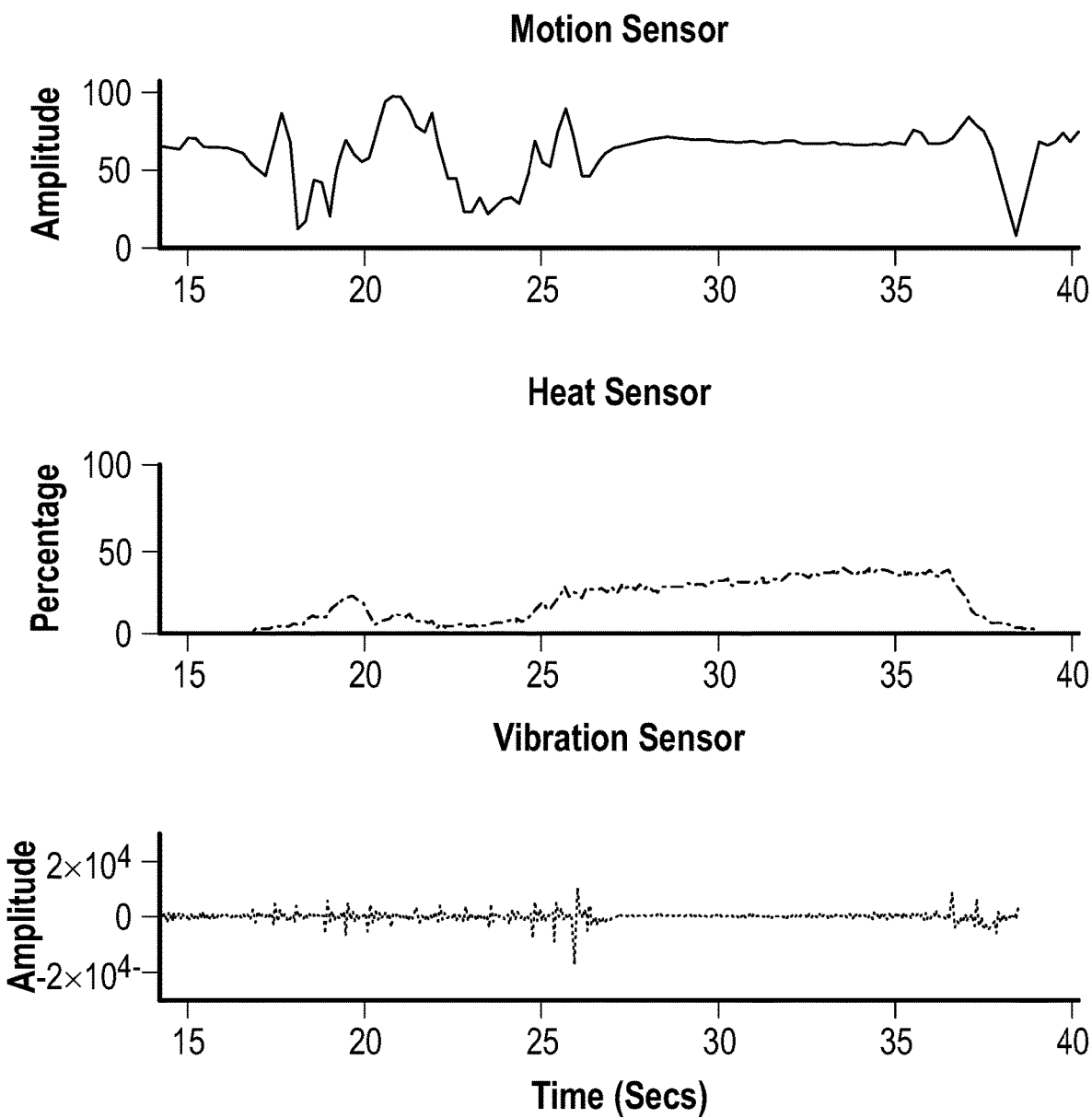
FIG. 19 depicts the output of an embodiment of a system, including the output before, during, and after a fall of a human.

This represented a scenario where a person inside a room dropped an object while walking, and then stopped walking, hence the word "freeze." In this case, the motion sensor detected a motion-to-stationary transition. It was found that even 20-pound objects did not cause vibrations as large as those of a typical human fall at the same distance to the sensor. As a result, the system still did not declare a fall, because it selected the correct vibration threshold which was higher than the vibration caused by the drop. In addition, in many cases, the human was still within the view of the heat sensor after the drop, which further prevented a fall from being declared. An example is seen in FIG. 19, in which a 20 pound object was dropped at around 26 seconds. Even when the vibration sensor picked up a fairly large vibration, the heat sensor detected many human pixels and considered the person to be standing.

D. Normal Jumping and Stomping

Figure 20:
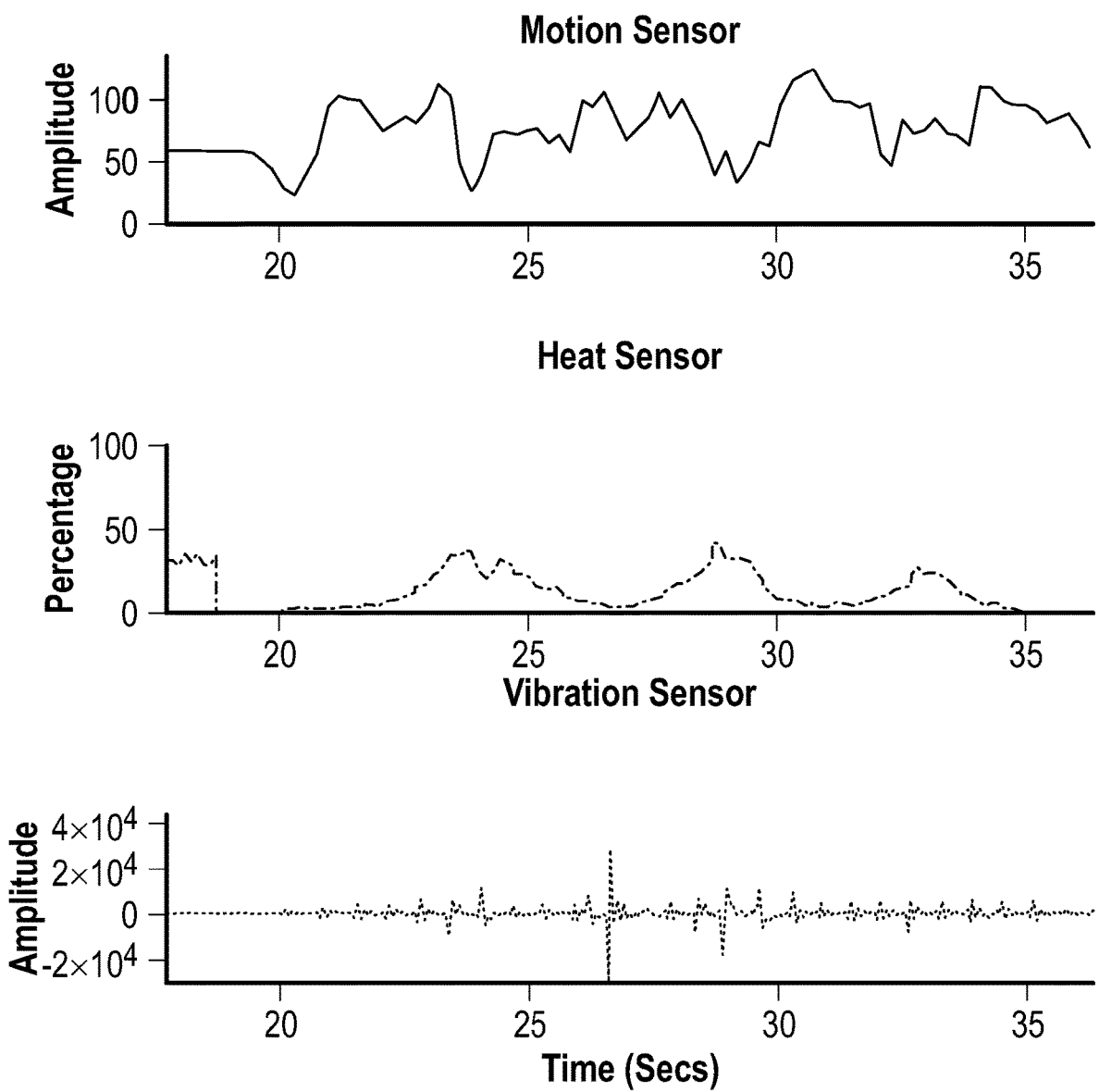
FIG. 20 depicts the output of an embodiment of a system, including the output before, during, and after a fall of a human.

This represented a scenario where a person, while walking inside the room, suddenly jumped or stomped, and then continued walking. Although the heat sensor did or did not detect the person, and the vibration sensor registered some relatively large vibration value, the system did not declare a fall, because the motion sensor did not register a stationary period after the jump or stomp and determined that the person was still in motion, such as the example in FIG. 20.

E. Close Freeze Jumping or Hard Stomping

Figure 21:
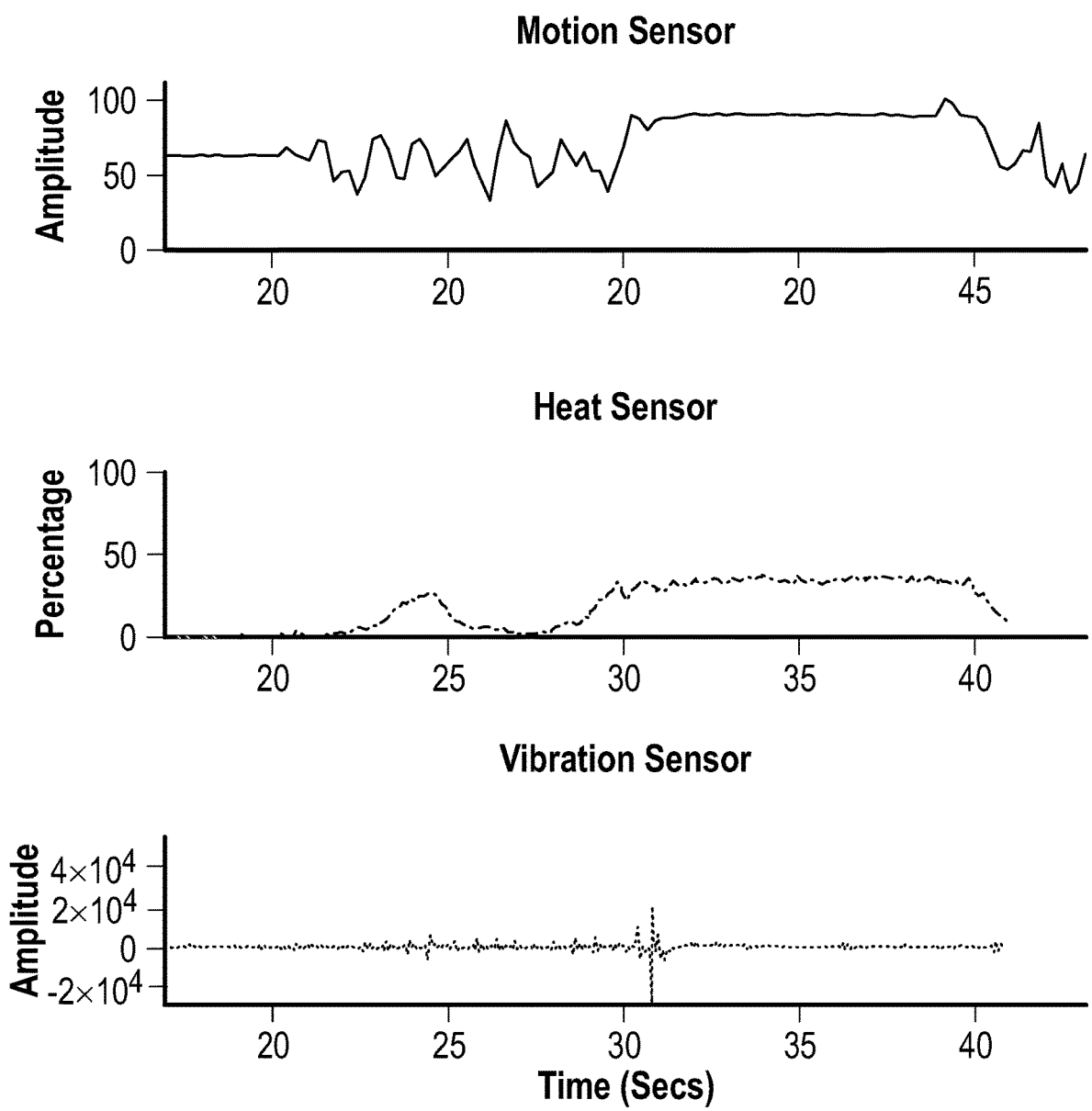
FIG. 21 depicts the output of an embodiment of a system, including the output before, during, and after a fall of a human.

This represented a scenario where a person was initially walking, then jumped or stomped hard at a location in view of the heat sensor, and then stood still. The system did not consider it a fall because although a motion-to-stationary transition occurred and the vibration sensor likely registered a large vibration value, the heat sensor still detected the human, for example, as shown in FIG. 21. Note that the stomping was significant because light stomping did not create vibrations larger than the threshold. The system declared a fall only if the human stayed still after the jump or stomp for over 30 seconds, which is an extremely unlikely scenario.

F. Far Freeze Jumping or Hard Stomping

Figure 22:
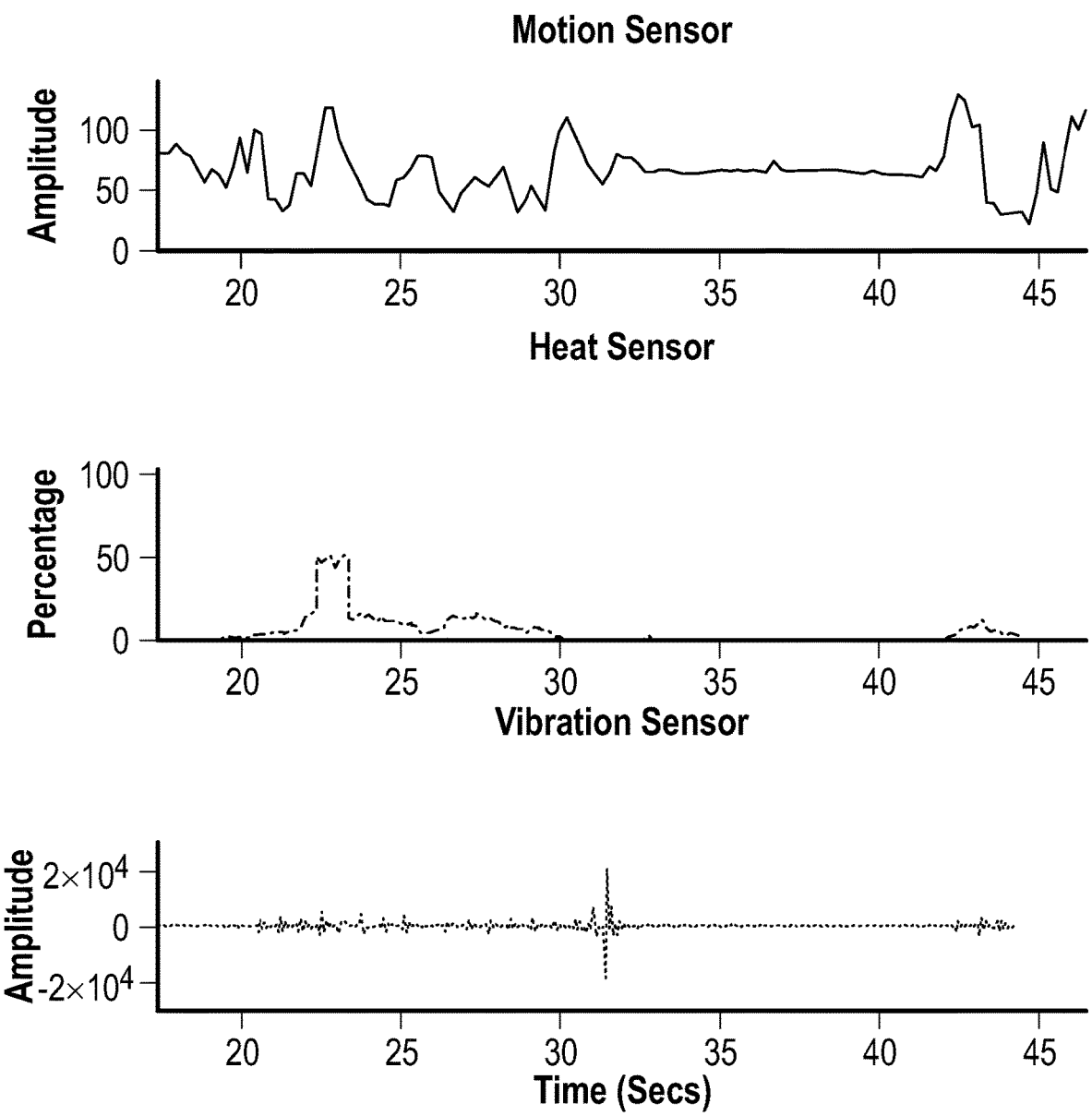
FIG. 22 depicts the output of an embodiment of a system, including the output before, during, and after a fall of a human.

This test represented a scenario where a person was initially walking, then jumped or stomped hard at a location outside the view of the heat sensor, and then stood still. In this case, the motion sensor detected a motion-to-stationary transition, the heat sensor detected the person, and the vibration sensor likely registered a large vibration value, such as that shown in FIG. 22. The system applied the smallest vibration threshold, and declared a fall in this case, as vibrations caused by the jump or a hard stomp were comparable to those caused by a human fall. However, this type of activity is unlikely to be engaged in by senior adults. Moreover, the devices, in some embodiments, can be placed at a location that reduces or minimizes blind spots.

Example 9—Selected Threshold Performance

The performance of the selected threshold of all the sensors of the system of Example 1 was tested in addition to the foregoing tests.

A. Motion Sensor

Figure 23:
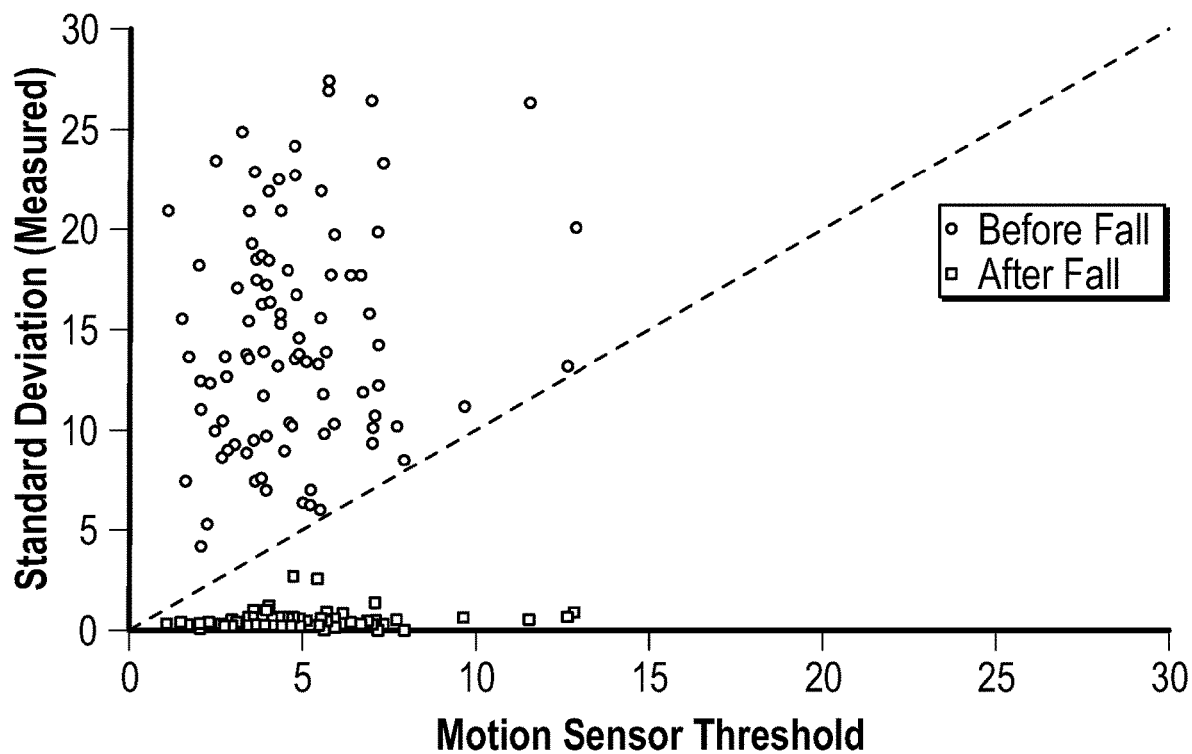
FIG. 23 depicts the calibration performance of an embodiment of a system, including the output before, and after a fall of a human.
Figure 24:
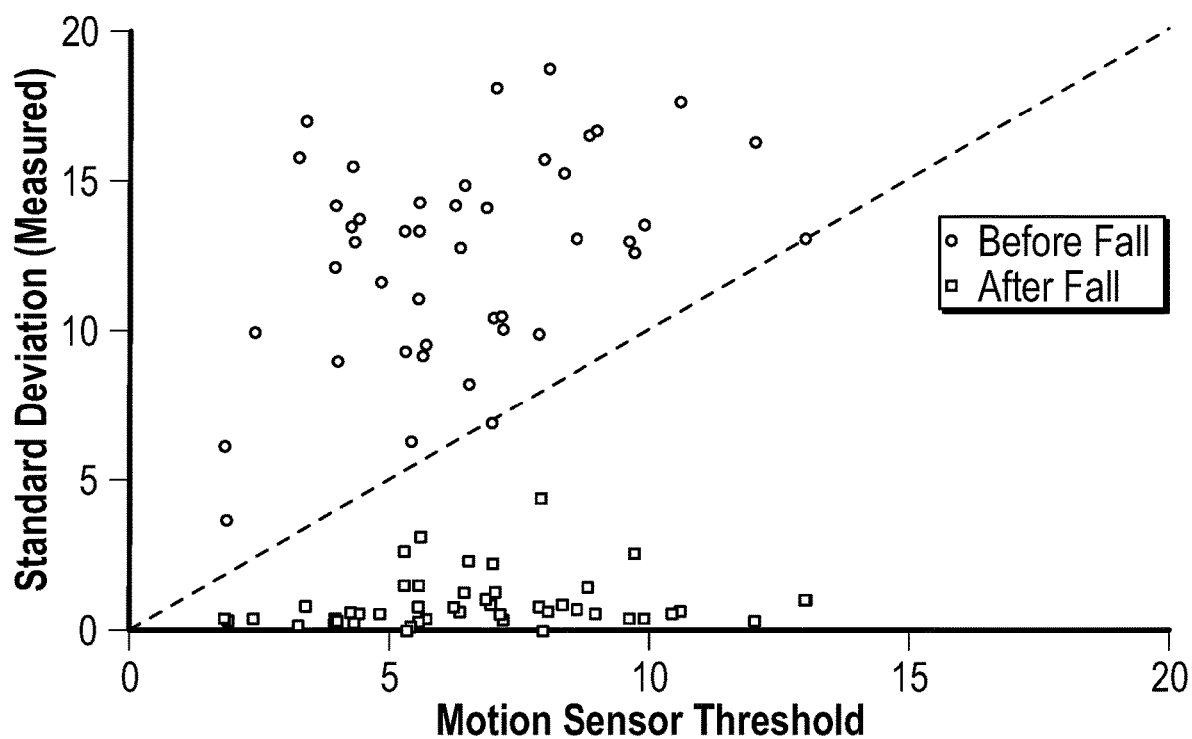
FIG. 24 depicts the calibration performance of an embodiment of a system, including the output before, and after a fall of a human.

The performance of the selected threshold of the motion sensor is seen in FIG. 23 and FIG. 24. Note that the first check of any potential fall was the motion-to-stationary transition. FIG. 23 is a scatter plot, where the x and y axis are the threshold for detecting motion and the variation of the motion sensor reading, respectively, and the readings before and after the fall are shown. The readings before a fall were all above the 45 degree diagonal line, while the readings after a fall were all below the line, which suggested that all fall events lead to detected motion-to-stationary transitions. FIG. 24 is also a scatter plot, showing the performance of the calibrated threshold in a bathroom environment.

B. Vibration Sensor

Figure 25:
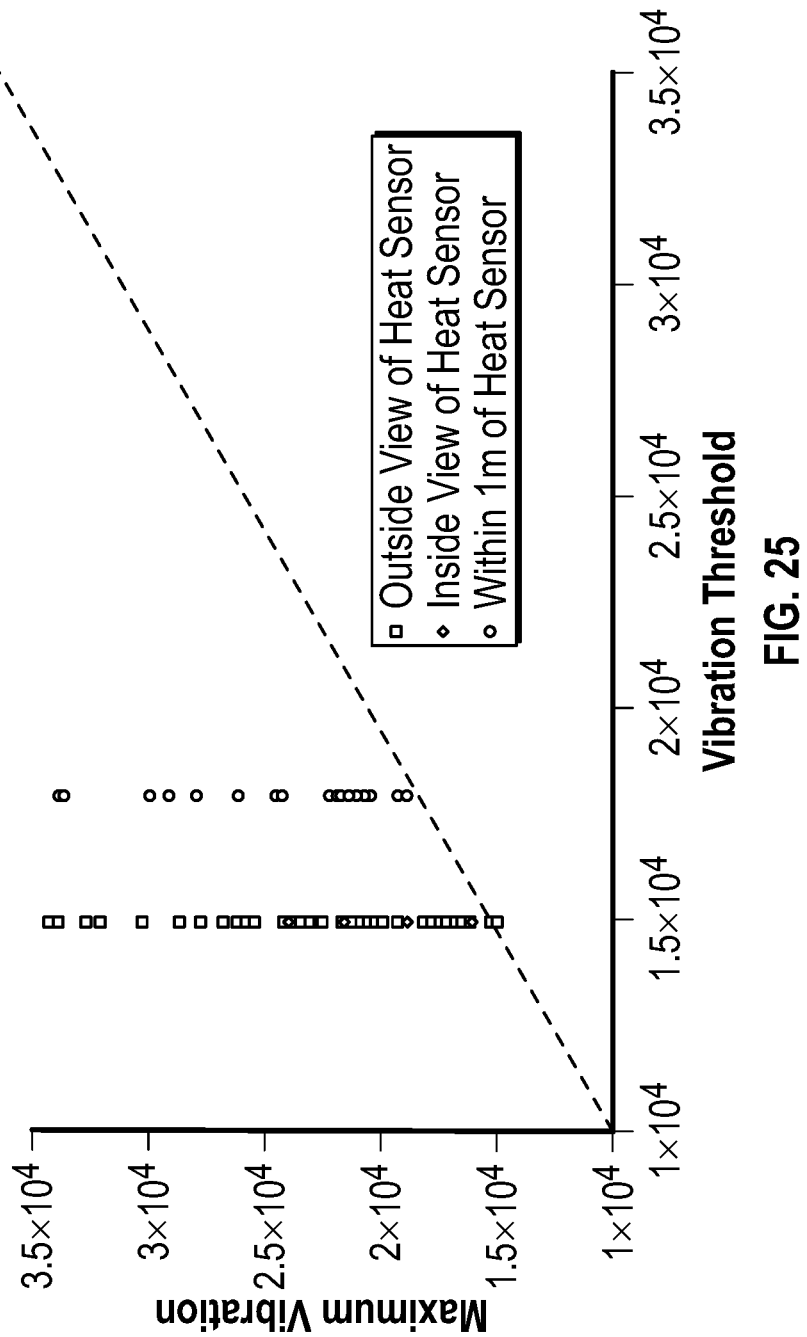
FIG. 25 depicts the calibration performance of an embodiment of a system, including the output before, and after a fall of a human.
Figure 26:
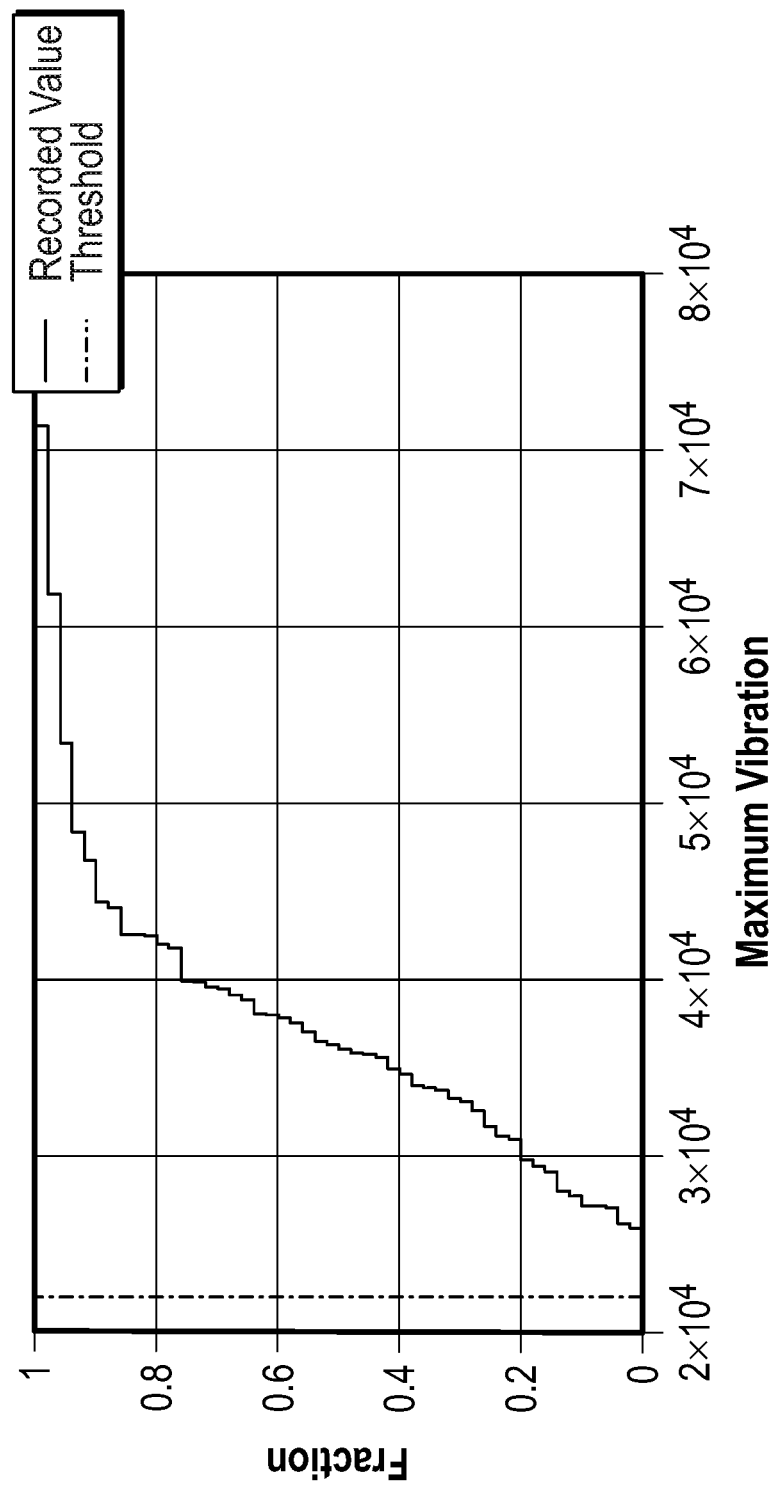
FIG. 26 depicts the calibration performance of an embodiment of a system, including the output before, and after a fall of a human.

In FIG. 25 and FIG. 26, the vibration sensor calibration performance is depicted. FIG. 25 is a scatter plot, where the x and y axis are the selected vibration threshold and the vibration reading of the falls, respectively. The vibration threshold was exceeded in all cases shown in the figure, suggesting that system in this example indeed selected the correct threshold values depending on the distances of the fall to the sensors. As the system used only 3 vibration threshold values obtained from calibration, the points appeared in three vertical lines. Only two lines are in the figure, because falls very close to the sensor lead to very large vibration readings and had to be cut off to show details in other cases.

FIG. 26 shows the Cumulative Density Function (CDF) plot of the vibration reading of the falls in a bathroom, in which the vertical line is the threshold. Only one threshold was used because the bathroom was small. The vibration threshold was exceeded in all cases.

We claim:

1. A method for detecting an occurrence of a fall of a human, the method comprising:
    providing a device comprising (i) a device body having a base configured for placement on a surface, (ii) a vibration sensor configured to detect vibrations of the surface, (iii) a motion sensor comprising a receiver configured to receive transmissions from one or more radio frequency transmitters, (iv) a heat sensor comprising a thermal camera, wherein the thermal camera comprises a plurality of pixels, and (v) a processing unit configured to (a) receive one or more signals from each of the motion sensor, the heat sensor, and the vibration sensor, and (b) determine an occurrence of an event based on the one or more signals received from the motion sensor, the heat sensor, and the vibration sensor, wherein the motion sensor, the heat sensor, the vibration sensor, and the processing unit are housed by the device body;
    detecting a motion-to-stationary transition of the human with the motion sensor;
    estimating a distance of the human from the heat sensor by determining a fraction of the plurality of pixels that detect a body temperature of the human;
    determining whether the human is standing after the motion-to-stationary transition based on a signal from the heat sensor; and
    declaring the occurrence of the fall if—
    [1] (i) the human is not standing after the motion-to-stationary transition, and (ii) a signal from the vibration sensor is greater than a threshold value based on the distance of the human from the heat sensor; or
    [2] (i) the signal from the heat sensor indicates that the human is standing after the motion-to-stationary transition, (ii) no movement is detected by the system for at least 10 seconds after the motion-to-stationary transition, and (iii) a signal from the vibration sensor is greater than a threshold value based on the distance of the human from the heat sensor.

2. A method for detecting an occurrence of a fall of a human, the method comprising:
    providing a device comprising (i) a device body having a base configured for placement on a surface, (ii) a vibration sensor configured to detect vibrations of the surface, (iii) a motion sensor comprising a receiver configured to receive transmissions from one or more radio frequency transmitters, (iv) a heat sensor comprising a thermal camera, wherein the thermal camera comprises a plurality of pixels, and (v) a processing unit configured to (a) receive one or more signals from each of the motion sensor, the heat sensor, and the vibration sensor, and (b) determine an occurrence of an event based on the one or more signals received from the motion sensor, the heat sensor, and the vibration sensor, wherein the motion sensor, the heat sensor, the vibration sensor, and the processing unit are housed by the device body;

detecting a motion-to-stationary transition of the human with the motion sensor;

estimating a distance of the human from the heat sensor by comparing a first signal and a second signal received by the processing unit from the heat sensor before and after the motion-to-stationary transition, respectively;

determining whether the second signal indicates that the human is standing after the motion-to-stationary transition; and declaring the occurrence of the fall if (i) the human is not standing after the motion-to-stationary transition, and (ii) a third signal from the vibration sensor is greater than a threshold value based on the distance of the human from the heat sensor.

* * * * *